(12) United States Patent
Kinishi et al.

(10) Patent No.: US 11,945,769 B2
(45) Date of Patent: Apr. 2, 2024

(54) N,N'-DIARYLUREA DERIVATIVE, MANUFACTURING METHOD THEREOF, AND THERMOSENSITIVE RECORDING MATERIAL USING SAME

(71) Applicant: SANKO CO., LTD., Kurume (JP)

(72) Inventors: Ryoichi Kinishi, Ibaraki (JP); Yoshimi Ishibashi, Ibaraki (JP)

(73) Assignee: SANKO CO., LTD., Fukuoka (JP)

( * ) Notice: Subject to any disclaimer, the term of this patent is extended or adjusted under 35 U.S.C. 154(b) by 896 days.

(21) Appl. No.: 16/641,811

(22) PCT Filed: Aug. 10, 2018

(86) PCT No.: PCT/JP2018/030081
§ 371 (c)(1),
(2) Date: Feb. 25, 2020

(87) PCT Pub. No.: WO2019/044462
PCT Pub. Date: Mar. 7, 2019

(65) Prior Publication Data
US 2021/0340099 A1    Nov. 4, 2021

(30) Foreign Application Priority Data
Aug. 31, 2017  (JP) ................. 2017-167444

(51) Int. Cl.
| | | |
|---|---|---|
| *B41M 5/20* | (2006.01) | |
| *B41M 5/24* | (2006.01) | |
| *B41M 5/323* | (2006.01) | |
| *C07C 303/28* | (2006.01) | |
| *C07C 303/30* | (2006.01) | |
| *C07C 309/76* | (2006.01) | |

(52) U.S. Cl.
CPC .......... *C07C 309/76* (2013.01); *B41M 5/323* (2013.01); *C07C 303/28* (2013.01); *C07C 303/30* (2013.01)

(58) Field of Classification Search
CPC ............... C07C 309/76; C07C 303/28; C07C 303/30; C07C 309/73; B41M 5/323; B41M 5/327; B41M 5/3275; B41M 5/3333; B41M 5/333
See application file for complete search history.

(56) References Cited

U.S. PATENT DOCUMENTS

| | | | |
|---|---|---|---|
| 2,787,574 A * | 4/1957 | Basso ............... | A61K 31/17 514/157 |
| 3,539,375 A | 11/1970 | Baum | |
| 5,541,224 A | 7/1996 | O'Doherty | |
| 9,518,011 B2 | 12/2016 | Sakai et al. | |
| 2002/0188027 A1 | 12/2002 | Robinson et al. | |
| 2013/0287700 A1 * | 10/2013 | Schmidt ............. | G01N 33/6896 544/242 |
| 2015/0284321 A1 | 10/2015 | Sakai et al. | |
| 2018/0345710 A1 | 12/2018 | Miyanaga et al. | |

FOREIGN PATENT DOCUMENTS

| | | | |
|---|---|---|---|
| CN | 101316841 A | 12/2008 | |
| CN | 102797429 A | 11/2012 | |
| CN | 103221387 A | 7/2013 | |
| CN | 104024220 A | 9/2014 | |
| CN | 103221387 B | 11/2014 | |
| CN | 104797429 A | 7/2015 | |
| JP | 60-208286 A | 10/1985 | |
| JP | 3-36086 A | 2/1991 | |
| JP | H0336086 A | 2/1991 | |
| JP | 9-510457 A | 10/1997 | |
| JP | 2002-052842 A | 2/2002 | |
| JP | 2002-532441 A | 10/2002 | |
| JP | 2010-053128 A | 3/2010 | |
| JP | 57-11088 B2 | 4/2015 | |
| WO | 2000/35679 A1 | 6/2000 | |
| WO | WO-2012037928 A2 * | 3/2012 | ........... A61K 31/426 |
| WO | WO-2016127085 A1 * | 8/2016 | ............... A61P 19/00 |

(Continued)

OTHER PUBLICATIONS

Chinese Office Action for Application No. 201880054951.3, dated Sep. 18, 2021, 9 pages.
Yang et al., The Development of Heat-sensitive CTP Plates of Fuji Photo Film Co. Based on the Patents. Information Recording Materials. 2003;4(1):24-28.
International Search Report and Written Opinion for Application No. PCT/JP2018/030081, dated Sep. 4, 2018, 9 pages.

*Primary Examiner* — Michael G. Hartley
*Assistant Examiner* — Melissa J Perreira
(74) *Attorney, Agent, or Firm* — McCarter & English, LLP; David R. Burns; Wei Song

(57) ABSTRACT

The present invention relates to an N,N'-diurea derivative represented by the following general formula (1) and a method for producing the same. In addition, the present invention relates to a thermosensitive recording material in which a thermosensitive recording layer including a basic dye which is colorless or lightly colored at room temperature and a developer capable of developing color upon contact with the basic dye by heating is provided on a base sheet, wherein the developer is the N,N'-diurea derivative represented by the following general formula (1):

[Chem. 1]

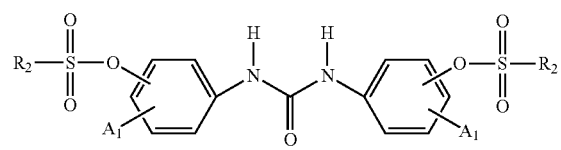

(1)

(wherein $R_2$ is an alkyl group, an aralkyl group, or an aryl group; and $A_1$ is a hydrogen atom or an alkyl group).

11 Claims, 10 Drawing Sheets

(56) References Cited

FOREIGN PATENT DOCUMENTS

WO       2014/080615 A1    1/2017
WO       2017/111032 A1   10/2018

\* cited by examiner

N,N'-DIARYLUREA DERIVATIVE, MANUFACTURING METHOD THEREOF, AND THERMOSENSITIVE RECORDING MATERIAL USING SAME

CROSS-REFERENCE TO RELATED APPLICATIONS

This application is a U.S. national stage filing, under 35 U.S.C. § 371(c), of International Application No. PCT/JP2018/030081, filed on Aug. 10, 2018, which claims priority of Japanese Patent Application No. 2017-167444, filed on Aug. 31, 2017. The entire contents of each of the aforementioned applications are incorporated herein by reference.

TECHNICAL FIELD

The present invention relates to an N,N'-diarylurea derivative, a method for producing the same, and a thermosensitive recording material using the same as a developer.

BACKGROUND ART

In general, a thermosensitive recording material is a product produced by respectively pulverizing and dispersing a colorless to pale basic dye and an organic developer into fine particles at room temperature, subsequently mixing both the fine particles mentioned above together with a sensitizer, a binder, a lubricant, and various other additives to obtain a coating liquid, and applying the coating liquid thus obtained on a base sheet such as paper, a plastic film, processed paper, or the like to form a thermal recording layer. The thermosensitive recording material to which heat energy from a thermosensitive head, a heat pen, or the like is applied to obtain color recording is already widely put into practical use. In addition, a thermosensitive recording material containing a light-conversion substance which absorbs laser light and converts it into heat is also widely used.

Such a thermosensitive recording material has advantages such that a recorded image can be obtained with a relatively simple device, for which maintenance is easy and that does not generate noise. For this reason, the thermosensitive recoding material is used in a wide range of applications such as a measurement recorder, a facsimile, various types of printers, a label printer, and a ticketing machine for passenger-tickets or tickets.

As examples of the performance required for the thermosensitive recording material, mention may be made of a whiteness of an unprinted portion, and a whiteness of the unprinted portion under various environmental conditions, a color density of a printed portion, storability of the printed portion, and the like. In particular, with respect to the storability of the printed portion, various tests such as moisture and heat resistance, water resistance, light resistance, oil resistance, and plasticizer resistance are required.

Heretofore, many developers have been proposed as developers for thermosensitive recording materials. For example, phenol-based developers such as 4,4'-isopropylidenediphenol (See U.S. Pat. No. 3,539,375), 4,4' dihydroxydiphenylsulfone (See Japanese Unexamined Patent Application, First Publication No. Sho 57-11088), 4-allyloxy-4'-hydroxy-diphenylsulfone (See Japanese Unexamined Patent Application, First Publication No. Sho 60-208286), 4-hydroxy-4'-isopropyloxy-diphenylsulfone (See Japanese Unexamined Patent Application, First Publication No. 2002-052842), and the like, and non-phenol-based developers such as N-3-[(p-toluenesulfonyl) oxy] phenyl-N'-(p-toluenesulfonyl)-urea (See Published Japanese Translation No. 2002-532441 of the PCT International Publication), N-[2-(3-phenylureido) phenyl]-benzenesulfonamide (See WO2014/080615), and the like have been proposed.

SUMMARY OF INVENTION

However, in the case of the phenol-based developers, various types of storage stability in printed portions and non-printed portions are not sufficient. N-3-[(p-toluenesulfonyl) oxy] phenyl-N'-(p-toluenesulfonyl)-urea, which is a non-phenol-based developer, has the improved color development sensitivity and the improved storage stability, but they are not sufficient, and further improvement is required. In addition, N-3-(p-toluenesulfonyloxy) phenyl-N'-(p-toluenesulfonyl)-urea has two functional groups of a toluenesulfonylurea group derived from toluenesulfonyl isocyanate and an aromatic sulfonic acid aryl ester group derived from toluenesulfonyl chloride. While the aromatic sulfonic acid aryl ester group is stable in water, the toluenesulfonylurea group as another functional group is originally used as a protective group for an amino group and the like, but has a disadvantage that it is easily hydrolyzed by water.

On the other hand, N-[2-(3-phenylureido) phenyl]-benzenesulfonamide still has a problem of storability of the recorded portion, and thus a required performance as a thermosensitive recording material cannot be sufficiently satisfied. A further improvement in the storage stability of the printed portion is required.

Usages of thermosensitive recording materials have been expanded, and the thermosensitive recording materials have been used in receipts for gas, water, and electricity bills, ATM usage statements for financial institutions, financial recording sheets, theater tickets, lottery tickets, voting tickets such as gaming ticket sheets for horse racing and boat racing tickets, tickets and receipts for railway and bus, air tag sheets, logistic-related label sheets, food label sheets such as prepared dishes and rice balls, POS cash register sheets for convenience stores and supermarkets, medical labels, electrocardiogram sheets, thermosensitive film for use in medical diagnosis, transportation commuter pass, and the like. Various properties are required depending on the usages.

In addition, in recent years, with respect to 4,4'-isopropylidenediphenol and 4,4'-bisphenol sulfone, problems in environmental health such as environmental hormones and mutagenicity have been pointed out. For this reason, in fact, there is a need for a non-phenol-based developer having no problems described above.

The present invention has been made in view of the circumstances mentioned above, and provides N,N'-diphenylurea derivatives which do not contain a phenol compound that is a concern for environmental health, and satisfies the required performance as a thermosensitive recording material, such as color density, whiteness, and storability of the printed portion, as well as provides a method for producing the same and a thermosensitive recording material using the same as a developer.

As a result of diligent studies, the present inventors have succeeded in producing a novel N,N'-diphenylurea derivative of the present invention, and have discovered that such a compound can be utilized as a color developer for thermosensitive recording materials. Thereby, the present invention has been completed.

That is, the present invention includes the aspects described below.

[1] An N,N'-diarylurea derivative represented by the following general formula (1):

[Chem. 1]

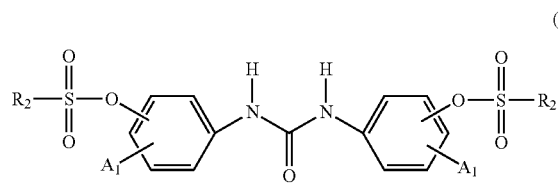

(1)

(wherein R2 is a linear, branched or alicyclic alkyl group having 1 to 12 carbon atoms, or an aralkyl group having 7 to 12 carbon atoms or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom, and a plurality of R2s may be the same or different. A1 represents a hydrogen atom, or an alkyl group having 1 to 4 carbon atoms. A plurality of A1s may be the same or different.)

[2] The N,N'-diarylurea derivative according to [1], which is represented by the following general formula (2):

[Chem. 2]

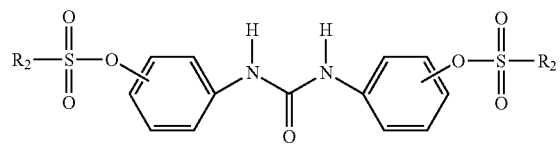

(2)

(wherein R2 is a linear, branched or alicyclic alkyl group having 1 to 12 carbon atoms, or an aralkyl group having 7 to 12 carbon atoms or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom, and a plurality of R2s may be the same or different.)

[3] The N,N'-diarylurea derivative according to [2], which is represented by the following general formula (3):

[Chem. 3]

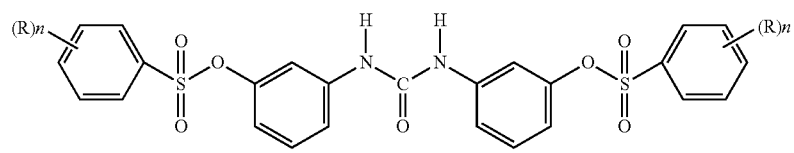

(3)

(wherein R represents an alkyl group, and n represents an integer ranging from 0 to 3.)

[4] A method for producing the N,N'-diarylurea derivative as described in any one of [1] to [3], including reacting a compound represented by the following general formula (4) with an aromatic amine compound represented by the following general formula (5).

[Chem. 4]

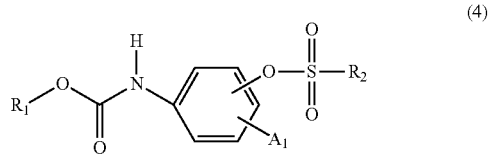

(4)

[Chem. 5]

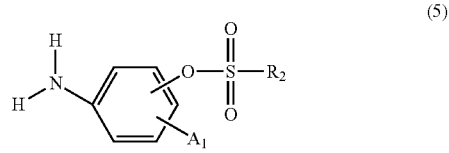

(5)

(wherein R1 represents an alkyl group or an aryl group. A1 represents a hydrogen atom, or an alkyl group having 1 to 4 carbon atoms. A plurality of A1s may be the same or different. R2 is a linear, branched or alicyclic alkyl group having 1 to 12 carbon atoms, or an aralkyl group having 7 to 12 carbon atoms or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom.)

[5] A method for producing the N,N'-diarylurea derivative as described in [3], including reacting a compound represented by the following general formula (6) with an aromatic amine compound represented by the following general formula (7).

[Chem. 6]

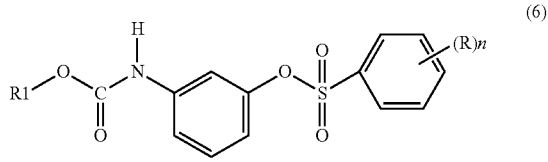

(6)

[Chem. 7]

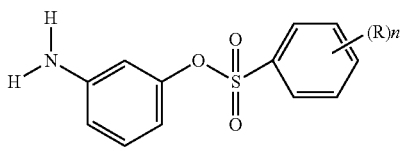

(7)

(wherein R1 represents an alkyl group or an aryl group, R represents an alkyl group, and n represents an integer ranging from 0 to 3.)

[6] A method for producing the N,N'-diarylurea derivative as described in any one of [1] to [3], including reacting a dihydroxydiphenylurea represented by the following general formula (8) with a sulfonating agent represented by the following general formula (9) in the presence of an aprotic solvent.

[Chem. 8]

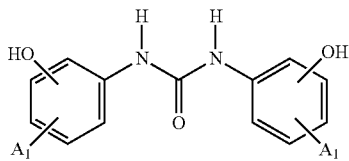

(8)

(wherein A1 represents a hydrogen atom, or an alkyl group having 1 to 4 carbon atoms. A plurality of A1s may be the same or different.)

[Chem. 9]

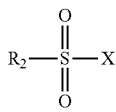

(9)

(wherein R2 is a linear, branched or alicyclic alkyl group having 1 to 12 carbon atoms, or an aralkyl group having 7 to 12 carbon atoms or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom. X is a halogen atom.)

[7] A method for producing the N,N'-diarylurea derivative as described in any one of [1] to [3], including reacting an aminophenol compound represented by the following general formula (8-1) with urea in the presence of an aprotic solvent, and subsequently reacting with a sulfonating agent represented by the following general formula (9):

[Chem. 10]

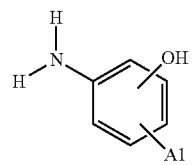

(8-1)

(wherein A1 represents a hydrogen atom, or an alkyl group having 1 to 4 carbon atoms.)

[Chem. 11]

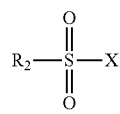

(9)

(wherein R2 is a linear, branched or alicyclic alkyl group having 1 to 12 carbon atoms, or an aralkyl group having 7 to 12 carbon atoms or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom. X is a halogen atom.)

[8] The method for producing the N,N'-diarylurea derivative according to [6] or [7], wherein the aprotic solvent is butyl acetate, amyl acetate, isoamyl acetate, toluene or xylene.

[9] A thermosensitive recording material in which a thermosensitive recording layer including a basic dye which is colorless or light-colored at room temperature and a developer capable of developing color upon contact with the basic dye mentioned above by heating is provided on a base sheet, wherein the aforementioned developer is the N,N'-diarylurea derivative as described in any one of [1] to [3].

Advantageous Effects of the Invention

By means of using the novel N,N'-diarylurea derivative represented by the aforementioned general formula (1) of the present invention as a developer, a thermosensitive recording material which does not contain a phenol compound having environmental health concerns and has improvements in color density, whiteness, and storability in the printed portion, can be provided.

EMBODIMENTS OF THE INVENTION (N,N'-Diarylurea Derivative)

Figure 1:
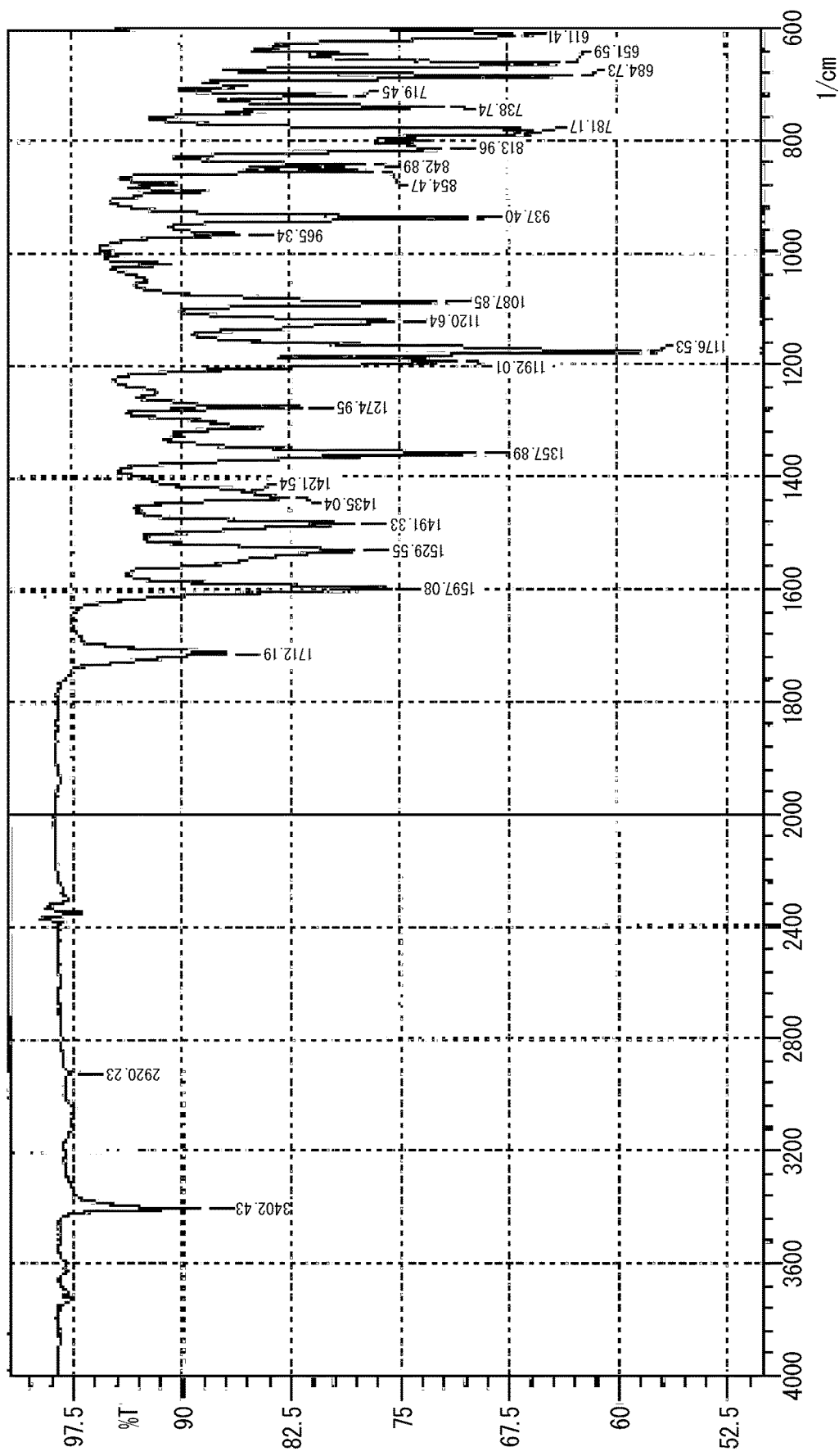
FIG. 1 shows an IR chart of N,N'-di-[3-(p-toluenesulfonyloxy) phenyl] urea (Synthesis Example 1) according to the present invention.

The N,N'-diarylurea derivative of the present invention is represented by general formula (1), general formula (2), or general formula (3).

In general formula (1) and general formula (2), R2 is a linear, branched or alicyclic alkyl group having 1 to 12 carbon atoms, or an aralkyl group having 7 to 12 carbon atoms, or an aryl group having 6 to 12 carbon atoms, which is unsubstituted or substituted with an alkyl group having 1 to 12 carbon atoms, an alkoxy group having 1 to 12 carbon atoms, an aryl group having 6 to 12 carbon atoms, or a halogen atom, and a plurality of R2s may be the same or different. A1 represents a hydrogen atom or an alkyl group having 1 to 4 carbon atoms. A plurality of A1s may be the same or different.

In general formula (3), R represents an alkyl group, and n represents an integer ranging from 0 to 3. The number of carbon atoms of the alkyl group of R may range from 1 to 12, may range from 1 to 8, or may range from 1 to 4.

In general formula (1), the substitution positions of a plurality of $R2-SO_3-$ may be the same substitution positions or different. The substitution positions are preferably the 3-position, 4-position, or 5-position, and more preferably the 3-position.

As examples of the linear, branched or alicyclic alkyl group having 1 to 12 carbon atoms of R2, mention may be made of linear, branched or alicyclic alkyl groups having 1 to 12 carbon atoms such as a methyl group, an ethyl group, an n-propyl group, an i-propyl group, an n-butyl group, an i-butyl group, a t-butyl group, a cyclopentyl group, a hexyl group, a cyclohexyl group, a 2-ethylhexyl group, a lauryl group and the like.

As examples of the aralkyl group, mention may be made of aralkyl groups which are unsubstituted or substituted with an alkyl group, an alkoxy group, an aralkyl group, an aryl group, or a halogen atom, such as a benzyl group, a 1-phenylethyl group, a 2-phenylethyl group, a 3-phenylpropyl group, a p-methylbenzyl group, an m-methylbenzyl group, an m-ethylbenzyl group, a p-ethylbenzyl group, a p-i-propylbenzyl group, a p-t-butylbenzyl group, a p-methoxybenzyl group, an m-methoxybenzyl group, an o-methoxybenzyl group, an m,p-di-methoxybenzyl group, a p-ethoxy-m-methoxybenzyl group, a p-phenylmethylbenzyl group, a p-cumylbenzyl group, a p-phenylbenzyl group, an o-phenylbenzyl group, an m-phenylbenzyl group, a p-tolylbenzyl group, an m-tolylbenzyl group, an o-tolylbenzyl group, a p-chlorobenzyl group, and the like.

As example of the aryl group, mention may be made of aryl groups which are unsubstituted or substituted with an alkyl group, an alkoxy group, an aralkyl group, an aryl group, or a halogen atom, such as a phenyl group, a p-tolyl group, an m-tolyl group, an o-tolyl group, a 2,5-dimethylphenyl group, a 2,4-dimethylphenyl group, a 3,5-dimethylphenyl group, a 2,3-dimethylphenyl group, a 3,4-dimethylphenyl group, a mesitylene group, a p-ethylphenyl group, a p-i-propylphenyl group, a p-t-butylphenyl group, a p-methoxyphenyl group, a 3,4-dimethoxyphenyl group, a p-ethoxyphenyl group, a p-chlorophenyl group, a 1-naphthyl group, a 2-naphthyl group, a t-butylated naphthyl group, and the like.

The substitution positions of a plurality of A1s may be the same substitution positions or different. The substitution positions are preferably the 3-position, the 4-position or the 5-position.

A1 is a hydrogen atom, or an alkyl group such as a methyl group, an ethyl group, a propyl group, an isopropyl group, a butyl group, an isobutyl group, a sec-butyl group, a t-butyl group, or the like.

As specific examples of the novel N,N'-diarylurea derivatives represented by the general formulae (1) to (3) of the present invention, the following compounds may be mentioned. However, the compounds are not limited to these compounds. In addition, two or more compounds may be used in combination as the developer.

In addition, by means of use of the novel N,N'-diarylurea derivatives in combination with the conventional developers such as a conventional non-phenol developer such as N-3-[(p-toluenesulfonyl) oxy] phenyl-N'-(p-toluenesulfonyl)-urea (trade name: PF-201), N-[2-(3-phenylureido) phenyl]-benzenesulfonamide (trade name: NKK-1304), or the like, a conventional developer such as 4,4'-isopropylidenediphenol (BPA), 4,4'-dihydroxydiphenylsulfone (BPS), 4-allyloxy-4'-hydroxydiphenylsulfone (trade name: BPS-MAE), 4-allyloxy-4'-hydroxy-diphenylsulfone (trade name: TGSA), 4-hydroxy-4'-isopropoxysulfone (trade name: D-8), N-(m-tolylaminocarbonyl)-methionine, N-(m-tolylaminocarbonyl)-phenylalanine, and N-(phenylaminocarbonyl)-phenylalanine, the storage stability that is a problem of these conventional developers can be further improved.

That is, as examples of the novel N,N'-diarylurea derivative of the present invention, the following compounds may be mentioned. N,N'-di-[3-(benzenesulfonyloxy) phenyl] urea, N,N'-di-[3-(benzenesulfonyloxy)-4-methyl-phenyl] urea, N,N'-di-[3-(benzenesulfonyloxy)-4-ethyl-phenyl] urea, N,N'-di-[3-(benzenesulfonyloxy)-5-methyl-phenyl] urea, N,N'-di-[3-(benzenesulfonyloxy)-4-propyl-phenyl] urea, N,N'-di-[3-(o-toluenesulfonyloxy) phenyl] urea, N,N'-di-[3-(m-toluenesulfonyloxy) phenyl] urea, N,N'-di-[3-(p-toluenesulfonyloxy) phenyl] urea, N,N'-di-[3-(p-toluenesulfonyloxy)-4-methyl-phenyl] urea, N,N'-di-[3-(p-xylenesulfonyloxy) phenyl] urea, N,N'-di-[3-(m-xylenesulfonyloxy) phenyl] urea, N,N'-di-[3-(mesitylenesulfonyloxy) phenyl] urea, N,N'-di-[3-(1-naphthalenesulfonyloxy) phenyl] urea, N,N'-di-[3-(2-naphthalenesulfonyloxy) phenyl] urea, N,N'-di-[3-(p-ethylbenzenesulfonyloxy) phenyl] urea, N,N'-di-[3-(p-propylbenzenesulfonyloxy) phenyl] urea, N,N'-di-[3-(p-isopropylbenzenesulfonyloxy) phenyl] urea, N,N'-di-[3-(p-t-butylbenzenesulfonyloxy) phenyl] urea, N,N'-di-[3-(p- methoxybenzenesulfonyloxy) phenyl] urea, N,N'-di-[3-(m-methoxybenzenesulfonyloxy) phenyl] urea, N,N'-di-[3-(o-methoxybenzenesulfonyloxy) phenyl] urea, N,N'-di-[3-(m,p-dimethoxybenzene sulfonyloxy) phenyl] urea, N,N'-di-[3-(p-ethoxybenzenesulfonyloxy) phenyl] urea, N,N'-di-[3-(p-propoxybenzenesulfonyloxy) phenyl] urea, N,N'-di-[3-(p-butoxybenzenesulfonyloxy) phenyl] urea, N,N'-di-[3-(p-cumylbenzylsulfonyloxy) phenyl] urea, N,N'-di-[3-(p-cumylbenzenesulfonyloxy) phenyl] urea, N,N'-di-[3-(o-phenylbenzenesulfonyloxy) phenyl] urea, N,N'-di-[3-(p-phenylbenzenesulfonyloxy) phenyl] urea, N,N'-di-[3-(p-chlorobenzenesulfonyloxy) phenyl] urea, N-[3-(benzenesulfonyloxy) phenyl]-N'-[3-(p-toluenesulfonyloxy) phenyl] urea, N-[3-(benzenesulfonyloxy) phenyl]-N'-[3-(m-toluenesulfonyloxy) phenyl] urea, N-[3-(benzenesulfonyloxy) phenyl]-N'-[3-(o-toluenesulfonyloxy) phenyl] urea, N-[3-(benzenesulfonyloxy) phenyl]-N'-[3-(p-xylenesulfonyloxy) phenyl] urea, N-[3-(benzenesulfonyloxy) phenyl]-N'-[3-(mesitylenesulfonyloxy) phenyl] urea, N-[3-(benzenesulfonyloxy) phenyl]-N'-[3-(1-naphthalenesulfonyloxy) phenyl] urea, N-[3-(benzenesulfonyloxy) phenyl]-N'-[3-(2-naphthalenesulfonyloxy) phenyl] urea, N-[3-(benzenesulfonyloxy) phenyl]-N'-[3-(p-ethylbenzenesulfonyloxy) phenyl] urea, N-[3-(benzenesulfonyloxy) phenyl]-N'-[3-(p-methoxybenzenesulfonyloxy) phenyl] urea, N-[3-(benzenesulfonyloxy) phenyl]-N'-[3-(benzylsulfonyloxy) phenyl] urea, N-[3-(benzenesulfonyloxy) phenyl]-N'-[3-(ethanesulfonyloxy) phenyl] urea, N-[3-(benzenesulfonyloxy) phenyl]-N'-[3-(benzenesulfonyloxy)-4-methylphenyl] urea, N-[3-(p-toluenesulfonyloxy) phenyl]-N'-[3-(m-toluenesulfonyloxy) phenyl] urea, N-[3-(p-toluenesulfonyloxy) phenyl]-N'-[3-(o-toluenesulfonyloxy) phenyl] urea, N-[3-(p-toluenesulfonyloxy) phenyl]-N'-[3-(p-toluenesulfonyloxy)-4-methylphenyl] urea, N-[3-(p-toluenesulfonyloxy) phenyl]-N'-[3-(p-ethylbenzenesulfonyloxy) phenyl] urea, N-[3-(p-toluenesulfonyloxy) phenyl]-N'-[3-(p-methoxybenzenesulfonyloxy) phenyl] urea, N-[3-(p-toluenesulfonyloxy) phenyl]-N'-[3-(2-naphthalenesulfonyloxy) phenyl] urea, N-[3-(p-toluenesulfonyloxy) phenyl]-N'-[3-(benzylsulfonyloxy) phenyl] urea, N-[3-(p-toluenesulfonyloxy) phenyl]-N'-[3-(p-methylbenzylsulfonyloxy) phenyl] urea, N-[3-(p-toluenesulfonyloxy) phenyl]-N'-[3-(p-methoxybenzylsulfonyloxy) phenyl] urea, N-[3-(p-toluenesulfonyloxy) phenyl]-N'-[3-(methanesulfonyloxy) phenyl] urea, N-[3-(p-toluenesulfonyloxy) phenyl]-N'-[3-(propanesulfonyloxy) phenyl] urea, N-[3-(p-toluenesulfonyloxy) phenyl]-N'-[3-(butanesulfonyloxy) phenyl] urea, N,N'-di-[3-(benzylsulfonyloxy) phenyl] urea, N,N'-di-[3-(benzylsulfonyloxy)-4-methyl-phenyl] urea, N,N'-di-[3-(phenylethanesulfonyloxy) phenyl] urea, N,N'-di-[3-(phenylpropanesulfonyloxy) phenyl] urea, N,N'-di-[3-(p-methoxybenzylsulfonyloxy) phenyl] urea, N-[3-(benzylsulfonyloxy) phenyl]-N'-[3-(p-methoxybenzylsulfonyloxy) phenyl] urea, N-[3-(benzylsulfonyloxy) phenyl]-N'-[3-(ethanesulfonyloxy) phenyl] urea, N-[3-(benzylsulfonyloxy) phenyl]-N'-[3-(butanesulfonyloxy) phenyl] urea, N,N'-di-[3-(methanesulfonyloxy) phenyl] urea, N,N'-di-[3-(methanesulfonyloxy)-4-methyl-phenyl] urea, N,N'-di-[3-(methanesulfonyloxy)-4-ethyl-phenyl] urea, N,N'-di-[3-(methanesulfonyloxy)-5-methyl-phenyl] urea, N,N'-di-[3-(methanesulfonyloxy)-4,5-dimethyl-phenyl] urea, N,N'-di-[3-(ethanesulfonyloxy) phenyl] urea, N,N'-di-[3-(ethanesulfonyloxy)-4-methyl-phenyl] urea, N,N'-di-[3-(1-propanesulfonyloxy) phenyl] urea, N,N'-di-[3-(2-propanesulfonyloxy) phenyl] urea, N,N'-di-[3 (butanesulfonyloxy) phenyl] urea, N,N'-di-[3-(pentanesulfonyloxy) phenyl] urea, N,N'-di-[3-(hexanesulfonyloxy) phenyl] urea, N,N'-di-[3-(cyclohexanesulfonyloxy) phenyl] urea, N,N'-di-[3-(dodecanesulfonyloxy) phenyl] urea, N-[3-(methanesulfonyloxy) phenyl]-N'-[3-(ethanesulfonyloxy) phenyl] urea, N-[3-(ethanesulfonyloxy) phenyl]-N'-[3-(propanesulfonyloxy) phenyl] urea, N-[3-(methanesulfonyloxy) phenyl]-N'-[3-(butanesulfonyloxy) phenyl] urea, N-[3-(ethanesulfonyloxy) phenyl]-N'-[3-(cyclohexanesulfonyloxy) phenyl] urea, N,N'-di-[4-(benzenesulfonyloxy) phenyl] urea, N,N'-di-[4-(benzenesulfonyloxy)-3-methyl-phenyl] urea, N,N'-di-[4-(benzenesulfonyloxy)-3-ethyl-phenyl] urea, N,N'-di-[4-(benzenesulfonyloxy)-3-propyl-phenyl] urea, N,N'-di-[4-(benzenesulfonyloxy)-3-t-butyl-phenyl] urea, N,N'-di-[4-(o-toluenesulfonyloxy) phenyl] urea, N,N'-di-[4-(m-toluenesulfonyloxy) phenyl] urea, N,N'-di-[4-(p-toluenesulfonyloxy) phenyl] urea, N,N'-di-[4-(p-toluenesulfonyloxy)-3-methyl-phenyl] urea, N,N'-di-[4-(p-xylenesulfonyloxy) phenyl] urea, N,N'-di-[4-(m-xylenesulfonyloxy) phenyl] urea, N,N'-di-[4-(mesitylenesulfonyloxy) phenyl] urea, N,N'-di-[4-(1-naphthalenesulfonyloxy) phenyl] urea, N,N'-di-[4-(2-naphthalenesulfonyloxy) phenyl] urea, N,N'-di-[4-(p-ethylbenzenesulfonyloxy) phenyl] urea, N,N'-di-[4-(p-propylbenzenesulfonyloxy) phenyl] urea, N,N'-di-[4-(p-isopropylbenzenesulfonyloxy) phenyl] urea, N,N'-di-[4-(p-t-butylbenzenesulfonyloxy) phenyl] urea, N,N'-di-[4-(p-methoxybenzenesulfonyloxy) phenyl] urea, N,N'-di-[4-(m-methoxybenzenesulfonyloxy) phenyl] urea, N,N'-di-[4-(o-methoxybenzenesulfonyloxy) phenyl] urea, N,N'-di-[4-(m,p-dimethoxybenzenesulfonyloxy) phenyl] urea, N,N'-di-[4-(p-ethoxybenzenesulfonyloxy) phenyl] urea, N,N'-di-[4-(p-propoxybenzenesulfonyloxy) phenyl] urea, N,N'-di-[4-(p-butoxybenzenesulfonyloxy) phenyl] urea, N,N'-di-[4-(p-cumylbenzylsulfonyloxy) phenyl] urea, N,N'-di-[4-(p-cumylbenzenesulfonyloxy) phenyl] urea, N,N'-di-[4-(o-phenylbenzenesulfonyloxy) phenyl] urea, N,N'-di-[4-(p-phenylbenzenesulfonyloxy) phenyl] urea, N,N'-di-[4-(p-chlorobenzenesulfonyloxy) phenyl] urea, N-[4-(benzenesulfonyloxy) phenyl]-N'-[4-(p-toluenesulfonyloxy) phenyl] urea, N-[4-(benzenesulfonyloxy) phenyl]-N'-[4-(m-toluenesulfonyloxy) phenyl] urea, N-[4-(benzenesulfonyloxy) phenyl]-N'-[4-(o-toluenesulfonyloxy) phenyl] urea, N-[4-(benzenesulfonyloxy) phenyl]-N'-[4-(p-xylenesulfonyloxy) phenyl] urea, N-[4-(benzenesulfonyloxy) phenyl]-N'-[4-(mesitylenesulfonyloxy) phenyl] urea, N-[4-(benzenesulfonyloxy) phenyl]-N'-[4-(1-naphthalenesulfonyloxy) phenyl] urea, N-[4-(benzenesulfonyloxy) phenyl]-N'-[4-(2-naphthalenesulfonyloxy) phenyl] urea, N-[4-(benzenesulfonyloxy) phenyl]-N'-[4-(p-ethylbenzenesulfonyloxy) phenyl] urea, N-[4-(benzenesulfonyloxy) phenyl]-N'-[4-(p-methoxybenzenesulfonyloxy) phenyl] urea, N-[4-(benzenesulfonyloxy) phenyl]-N'-[4-(benzylsulfonyloxy) phenyl] urea, N-[4-(benzenesulfonyloxy) phenyl]-N'-[4-(ethanesulfonyloxy) phenyl] urea, N-[4-(p-toluenesulfonyloxy) phenyl]-N'-[4-(m-toluenesulfonyloxy) phenyl] urea, N-[4-(p-toluenesulfonyloxy) phenyl]-N'-[4-(o-toluenesulfonyloxy) phenyl] urea, N-[4-(p-toluenesulfonyloxy) phenyl]-N'-[4-(p-ethylbenzenesulfonyloxy) phenyl] urea, N-[4-(p-toluenesulfonyloxy) phenyl]-N'-[4-(p-methoxybenzenesulfonyloxy) phenyl] urea, N-[4-(p-toluenesulfonyloxy) phenyl]-N'-[4-(2-naphthalenesulfonyloxy) phenyl] urea, N-[4-(p- toluenesulfonyloxy) phenyl]-N'-[4-(benzylsulfonyloxy) phenyl] urea, N-[4-(p-toluenesulfonyloxy) phenyl]-N'-[4-(p-methylbenzylsulfonyloxy) phenyl] urea, N-[4-(p-toluenesulfonyloxy) phenyl]-N'-[4-(p-methoxybenzylsulfonyloxy) phenyl] urea, N-[4-(p-toluenesulfonyloxy) phenyl]-N'-[4-(methanesulfonyloxy) phenyl] urea, N-[4-(p-toluenesulfonyloxy) phenyl]-N'-[4-(propanesulfonyloxy) phenyl] urea, N-[4-(p-toluenesulfonyloxy) phenyl]-N'-[4-(butanesulfonyloxy) phenyl] urea, N,N'-di-[4-(benzylsulfonyloxy) phenyl] urea, N,N'-di-[4-(benzylsulfonyloxy)-3-methyl-phenyl] urea, N,N'-di-[4-(phenylethanesulfonyloxy) phenyl] urea, N,N'-di-[4-(phenylpropanesulfonyloxy) phenyl] urea, N,N'-di-[4-(p-methoxybenzylsulfonyloxy) phenyl) urea, N-[4-(benzylsulfonyloxy) phenyl]-N'-[4-(methanesulfonyloxy) phenyl] urea, N-[4-(benzylsulfonyloxy) phenyl]-N'-[4-(ethanesulfonyloxy) phenyl] urea, N,N'-di-[4-(methanesulfonyloxy) phenyl] urea, N,N'-di-[4-(methanesulfonyloxy)-3-methyl-phenyl] urea, N,N'-di-[4-(methanesulfonyloxy)-4-ethyl-phenyl] urea, N,N'-di-[4-(methanesulfonyloxy)-3-methyl-phenyl] urea, N,N'-di-[4-(methanesulfonyloxy)-3,5-dimethyl-phenyl] urea, N,N'-di-[4-(ethanesulfonyloxy) phenyl] urea, N,N'-di-[4-(ethanesulfonyloxy)-3-methyl-phenyl] urea, N,N'-di-[4-(1-propanesulfonyloxy) phenyl] urea, N,N'-di-[4-(2-propanesulfonyloxy) phenyl] urea, N,N'-di-[4-butanesulfonyloxy) phenyl] urea, N,N'-di-[4-(pentanesulfonyloxy) phenyl] urea, N,N'-di-[4-(hexanesulfonyloxy) phenyl] urea, N,N'-di-[4-(cyclohexanesulfonyloxy) phenyl] urea, N,N'-di-[4-(dodecanesulfonyloxy) phenyl] urea, N-[4-(methanesulfonyloxy) phenyl]-N'-[4-(ethanesulfonyloxy) phenyl] urea, N-[4-(methanesulfonyloxy) phenyl]-N'-[4-(propanesulfonyloxy) phenyl] urea, N,N'-di-[2-(benzenesulfonyloxy) phenyl] urea, N,N'-di-[2-(benzenesulfonyloxy)-4-methyl-phenyl] urea, N,N'-di-[2-(benzenesulfonyloxy)-4-ethyl-phenyl] urea, N,N'-di-[2-(benzenesulfonyloxy)-5-methyl-phenyl] urea, N,N'-di-[2-(benzenesulfonyloxy)-4-propyl-phenyl] urea, N,N'-di-[2-(o-toluenesulfonyloxy) phenyl] urea, N,N'-di-[2-(m-toluenesulfonyloxy) phenyl] urea, N,N'-di-[2-(p-toluenesulfonyloxy) phenyl] urea, N,N'-di-[2-(p-toluenesulfonyloxy)-4-methyl-phenyl] urea, N,N'-di-[2-(p-xylenesulfonyloxy) phenyl] urea, N,N'-di-[2-(m-xylenesulfonyloxy) phenyl] urea, N,N'-di-[2-(mesitylenesulfonyloxy) phenyl] urea, N,N'-di-[2-(1-naphthalenesulfonyloxy) phenyl] urea, N,N'-di-[2-(2-naphthalenesulfonyloxy) phenyl] urea, N,N'-di-[2-(p-ethylbenzenesulfonyloxy) phenyl] urea, N,N'-di-[2-(p-propylbenzenesulfonyloxy) phenyl] urea, N,N'-di-[2-(p-isopropylbenzene sulfonyloxy) phenyl] urea, N,N'-di-[2-(p-t-butylbenzenesulfonyloxy) phenyl] urea, N,N'-di-[2-(p-methoxybenzenesulfonyloxy) phenyl] urea, N,N'-di-[2-(m-methoxybenzenesulfonyloxy) phenyl] urea, N,N'-di-[2-(o-methoxybenzene sulfonyloxy) phenyl] urea, N,N'-di-[2-(m,p-dimethoxybenzene sulfonyloxy) phenyl] urea, N,N'-di-[2-(p-ethoxybenzene sulfonyloxy) phenyl] urea, N,N'-di-[2-(p-propoxybenzene sulfonyloxy) phenyl] urea, N,N'-di-[2-(p-butoxybenzene sulfonyloxy) phenyl] urea, N,N'-di-[2-(p-cumylbenzylsulfonyloxy) phenyl] urea, N,N'-di-[2-(p-cumylbenzenesulfonyloxy) phenyl] urea, N,N'-di-[2-(o-phenylbenzenesulfonyloxy) phenyl] urea, N,N'-di-[2-(p-phenylbenzenesulfonyloxy) phenyl] urea, N,N'-di-[2-(p-chlorobenzenesulfonyloxy) phenyl] urea, N-[2-(benzenesulfonyloxy) phenyl]-N'-[2-(p-toluenesulfonyloxy) phenyl] urea, N-[2-(benzenesulfonyloxy) phenyl]-N'-[2-(m-toluenesulfonyloxy) phenyl] urea, N-[2-(benzenesulfonyloxy) phenyl]-N'-[2-(o-toluenesulfonyloxy) phenyl] urea, N-[2-(benzenesulfonyloxy) phenyl]-N'-[2-(p-xylenesulfonyloxy) phenyl] urea, N-[2-(benzenesulfonyloxy) phenyl]-N'-[2-(mesitylenesulfonyloxy) phenyl] urea, N-[2-(benzenesulfonyloxy) phenyl]-N'-[2-(1-naphthalenesulfonyloxy) phenyl] urea, N-[2-(benzenesulfonyloxy) phenyl]-N'-[2-(2-naphthalenesulfonyloxy) phenyl] urea, N-[2-(benzenesulfonyloxy) phenyl]-N'-[2-(p-ethylbenzenesulfonyloxy) phenyl] urea, N-[2-(benzenesulfonyloxy) phenyl]-N'-[2-(p-methoxybenzenesulfonyloxy) phenyl] urea, N-[2-(benzenesulfonyloxy) phenyl]-N'-[2-(benzylsulfonyloxy) phenyl] urea, N-[2-(benzenesulfonyloxy) phenyl]-N'-[2-(ethanesulfonyloxy) phenyl] urea, N-[2-(p-toluenesulfonyloxy) phenyl]-N'-[2-(m-toluenesulfonyloxy) phenyl] urea, N-[2-(p-toluenesulfonyloxy) phenyl]-N'-[2-(o-toluenesulfonyloxy) phenyl] urea, N-[2-(p-toluenesulfonyloxy) phenyl]-N'-[2-(p-ethylbenzenesulfonyloxy) phenyl] urea, N-[2-(p-toluenesulfonyloxy) phenyl]-N'-[2-(p-methoxybenzenesulfonyloxy) phenyl] urea, N-[2-(p-toluenesulfonyloxy) phenyl]-N'-[2-(2-naphthalenesulfonyloxy) phenyl] urea, N-[2-(p-toluenesulfonyloxy) phenyl]-N'-[2-(benzylsulfonyloxy) phenyl] urea, N-[2-(p-toluenesulfonyloxy) phenyl]-N'-[2-(p-methylbenzylsulfonyloxy) phenyl] urea, N-[2-(p-toluenesulfonyloxy) phenyl]-N'-[2-(p-methoxybenzylsulfonyloxy) phenyl] urea, N-[2-(p-toluenesulfonyloxy) phenyl]-N'-[2-(methanesulfonyloxy) phenyl] urea, N-[2-(p-toluenesulfonyloxy) phenyl]-N'-[2-(propanesulfonyloxy) phenyl] urea, N-[2-(p-toluenesulfonyloxy) phenyl]-N'-[2-(butanesulfonyloxy) phenyl] urea, N,N'-di-[2-(benzylsulfonyloxy) phenyl] urea, N,N'-di-[2-(benzylsulfonyloxy)-4-methyl-phenyl] urea, N,N'-di-[2-(phenylethanesulfonyloxy) phenyl] urea, N,N'-di-[2-(phenylpropanesulfonyloxy) phenyl] urea, N, N'-di-[2-(p-methoxybenzylsulfonyloxy) phenyl] urea, and the like.

N-[2-(benzylsulfonyloxy) phenyl]-N'-[2-(propanesulfonyloxy) phenyl] urea, N-[2-(benzylsulfonyloxy) phenyl]-N'-[2-(p-methoxybenzylsulfonyloxy) phenyl] urea, N,N'-di-[2-(methanesulfonyloxy) phenyl] urea, N,N'-di-[2-(methanesulfonyloxy)-4-methyl-phenyl] urea, N,N'-di-[2-(methanesulfonyloxy)-4-ethyl-phenyl] urea, N,N'-di-[2-(methanesulfonyloxy)-5-methyl-phenyl] urea, N,N'-di-[2-(methanesulfonyloxy)-4,5-dimethyl-phenyl] urea, N,N'-di-[2-(ethanesulfonyloxy) phenyl] urea, N,N'-di-[2-(ethanesulfonyloxy)-4-methyl-phenyl] urea, N,N'-di-[2-(1-propanesulfonyloxy) phenyl] urea, N,N'-di-[2-(2-propanesulfonyloxy) phenyl] urea, N,N'-di-[2-(butanesulfonyloxy) phenyl] urea, N,N'-di-[2-(pentanesulfonyloxy) phenyl] urea, N,N'-di-[2-(hexanesulfonyloxy) phenyl] urea, N,N'-di-[2-(cyclohexane sulfonyloxy) phenyl] urea, N,N'-di-[2-(dodecanesulfonyloxy) phenyl] urea, N-[2-(ethanesulfonyloxy) phenyl]-N'-[2-(propanesulfonyloxy) phenyl] urea, N-[2-(ethanesulfonyloxy) phenyl]-N'-[2-(hexanesulfonyloxy) phenyl] urea, N-[3-(benzenesulfonyloxy) phenyl]-N'-[4-(benzenesulfonyloxy) phenyl] urea, N-[3-(p-toluenesulfonyloxy) phenyl]-N'-[4'-(p-toluenesulfonyloxy) phenyl] urea, N-[3-(m-toluenesulfonyloxy) phenyl]-N'-[4-(m-toluenesulfonyloxy) phenyl] urea, N-[3-(o-toluenesulfonyloxy) phenyl]-N'-[3-(o-toluenesulfonyloxy) phenyl] urea, N-[3-(p-xylenesulfonyloxy) phenyl]-N'-[4-(p-xylenesulfonyloxy) phenyl] urea, N-[3-(m-xylenesulfonyloxy)

phenyl]-N'-[4-(m-xylenesulfonyloxy) phenyl] urea, N-[3-(mesitylenesulfonyloxy) phenyl]-N'-[4-(mesitylenesulfonyloxy) phenyl] urea, N-[3-(1-naphthalenesulfonyloxy) phenyl]-N'-[4-(1-naphthalenesulfonyloxy) phenyl] urea, N-[3-(2-naphthalenesulfonyloxy) phenyl]-N'-[3-(2-naphthalene sulfonyloxy) phenyl] urea, N-[3-(p-ethylbenzenesulfonyloxy) phenyl]-N'-[4-(p-ethylbenzenesulfonyloxy) phenyl] urea, N-[3-(p-propylbenzenesulfonyloxy) phenyl]-N'-[4-(p-propylbenzene sulfonyloxy) phenyl] urea, N-[3-(p-isopropylbenzenesulfonyloxy) phenyl]-N'-[4-(p-isopropylbenzenesulfonyloxy) phenyl] urea, N-[3-(p-t-butylbenzenesulfonyloxy) phenyl]-N'-[4-(p-t-butylbenzenesulfonyloxy) phenyl] urea, N-[3-(p-methoxybenzenesulfonyloxy) phenyl]-N'-[4-(p-methoxybenzene sulfonyloxy) phenyl] urea, N-[3-(m-methoxybenzenesulfonyloxy) phenyl]-N'-[4-(m-methoxybenzenesulfonyloxy) phenyl] urea, N-[3-(o-methoxybenzenesulfonyloxy) phenyl]-N'-[4-(o-methoxybenzenesulfonyloxy) phenyl] urea, N-[3-(m,p-dimethoxy benzenesulfonyloxy) phenyl]-N'-[4-(m,p-dimethoxybenzenesulfonyloxy) phenyl] urea, N-[3-(p-ethoxybenzenesulfonyloxy) phenyl]-N'-[4-(p-ethoxybenzenesulfonyloxy) phenyl] urea, N-[3-(p-propoxybenzenesulfonyloxy) phenyl]-N'-[4-(p-propoxybenzenesulfonyloxy) phenyl] urea, N-[3-(p-butoxybenzenesulfonyloxy) phenyl]-N'-[4-(p-butoxybenzenesulfonyloxy) phenyl] urea, N-[3-(p-cumylbenzylsulfonyloxy) phenyl]-N'-[4-(p-cumylbenzylsulfonyloxy) phenyl] urea, N-[3-(p-cumylbenzenesulfonyloxy) phenyl]-N'-[4-(p-cumylbenzene sulfonyloxy) phenyl] urea, N-[3-(o-phenylbenzenesulfonyloxy) phenyl]-N'-[4-(o-phenylbenzenesulfonyloxy) phenyl] urea, N-[3-(p-phenylbenzene sulfonyloxy) phenyl]-N'-[4-(p-phenylbenzenesulfonyloxy) phenyl] urea, N-[3-(p-chlorobenzenesulfonyloxy) phenyl]-N'-[4-(p-chlorobenzene sulfonyloxy) phenyl] urea, N-[3-(benzenesulfonyloxy) phenyl]-N'-[4-(p-toluenesulfonyloxy) phenyl] urea, N-[3-(p-toluenesulfonyloxy) phenyl]-N'-[4-(o-toluenesulfonyloxy) phenyl] urea, N-[3-(p-toluenesulfonyloxy) phenyl]-N'-[4-(benzenesulfonyloxy) phenyl] urea, N-[3-(benzenesulfonyloxy) phenyl]-N'-[4-(ethanesulfonyloxy) phenyl] urea, N-[3-(p-toluenesulfonyloxy) phenyl]-N'-[4-(benzylsulfonyloxy) phenyl] urea, N-[3-(benzylsulfonyloxy) phenyl]-N'-[4-(benzylsulfonyloxy) phenyl] urea, N-[3-(phenylethanesulfonyloxy) phenyl]-N'-[4-(phenylethanesulfonyloxy) phenyl] urea, N-[3-(phenylpropanesulfonyloxy) phenyl]-N'-[4-(phenylpropanesulfonyloxy) phenyl] urea, N-[3-(p-methoxybenzylsulfonyloxy) phenyl]-N'-[4-(p-methoxybenzyl sulfonyloxy) phenyl] urea, and the like.

N-[3-(benzylsulfonyloxy) phenyl]-N'-[4-(butanesulfonyloxy) phenyl] urea, N-[3-(benzylsulfonyloxy) phenyl]-N'-[4-(p-methylbenzylsulfonyloxy) phenyl] urea, N-[3-(methanesulfonyloxy) phenyl]-N'-[4-(methanesulfonyloxy) phenyl] urea, N-[3-(ethanesulfonyloxy) phenyl]-N'-[4-(ethanesulfonyloxy) phenyl] urea, N-[3-(1-propanesulfonyloxy) phenyl)-N'-[4-(1-propanesulfonyloxy) phenyl] urea, N-[3-(2-propanesulfonyloxy) phenyl]-N'-[4-(2-propanesulfonyloxy) phenyl] urea, N-[3-(butanesulfonyloxy) phenyl]-N'-[4-(butanesulfonyloxy) phenyl] urea, N-[3-(pentanesulfonyloxy) phenyl]-N'-[4-(pentanesulfonyloxy) phenyl] urea, N-[3-(hexanesulfonyloxy) phenyl]-N'-[4-(hexanesulfonyloxy) phenyl] urea, N-[3-(cyclohexanesulfonyloxy) phenyl]-N'-[4-(cyclohexanesulfonyloxy) phenyl] urea, N-[3-(dodecanesulfonyloxy) phenyl]-N'-[4-(dodecanesulfonyloxy) phenyl] urea, N-[3-(methanesulfonyloxy) phenyl]-N'-[4-(ethanesulfonyloxy) phenyl] urea, N-[3-(methanesulfonyloxy) phenyl]-N'-[4-(butanesulfonyloxy) phenyl] urea, N-[2-(benzenesulfonyloxy) phenyl]-N'-[4-(benzenesulfonyloxy) phenyl] urea, N-[2-(p-toluenesulfonyloxy) phenyl]-N'-[4-(p-toluenesulfonyloxy) phenyl] urea, N-[2-(m-toluenesulfonyloxy) phenyl]-N'-[4-(m-toluenesulfonyloxy) phenyl] urea, N-[2-(o-toluenesulfonyloxy) phenyl]-N'-[4-(o-toluenesulfonyloxy) phenyl] urea, N-[2-(p-xylenesulfonyloxy) phenyl]-N'-[4-(p-xylenesulfonyloxy) phenyl] urea, N-[2-(m-xylenesulfonyloxy) phenyl]-N'-[4-(m-xylenesulfonyloxy) phenyl] urea, N-[2-(mesitylenesulfonyloxy) phenyl]-N'-[4-(mesitylenesulfonyloxy) phenyl] urea, N-[2-(1-naphthalenesulfonyloxy) phenyl]-N'-[4-(1-naphthalenesulfonyloxy) phenyl] urea, N-[2-(2-naphthalenesulfonyloxy) phenyl]-N'-[4-(2-naphthalene sulfonyloxy) phenyl] urea, N-[2-(p-ethylbenzenesulfonyloxy) phenyl]-N'-[4-(p-ethylbenzenesulfonyloxy) phenyl] urea, N-[2-(p-propylbenzenesulfonyloxy) phenyl]-N'-[4-(p-propylbenzene sulfonyloxy) phenyl] urea, N-[2-(p-isopropylbenzenesulfonyloxy) phenyl]-N'-[4-(p-isopropylbenzenesulfonyloxy) phenyl] urea, N-[2-(p-t-butylbenzenesulfonyloxy) phenyl]-N'-[4-(p-t-butylbenzenesulfonyloxy) phenyl] urea, N-[2-(p-methoxybenzenesulfonyloxy) phenyl]-N'-[4-(p-methoxybenzene sulfonyloxy) phenyl] urea, N-[2-(m-methoxybenzenesulfonyloxy) phenyl]-N'-[4-(m-methoxybenzenesulfonyloxy) phenyl] urea, N-[2-(o-methoxybenzenesulfonyloxy) phenyl]-N'-[4-(o-methoxybenzenesulfonyloxy) phenyl] urea, N-[2-(m,p-dimethoxy benzenesulfonyloxy) phenyl]-N'-[4-(m,p-dimethoxybenzenesulfonyloxy) phenyl] urea, N-[2-(p-ethoxybenzenesulfonyloxy) phenyl]-N'-[4-(p-ethoxybenzenesulfonyloxy) phenyl] urea, N-[2-(p-propoxybenzenesulfonyloxy) phenyl]-N'-[4-(p-propoxybenzene sulfonyloxy) phenyl] urea, N-[2-(p-butoxybenzenesulfonyloxy) phenyl]-N'-[4-(p-butoxybenzenesulfonyloxy) phenyl] urea, N-[2-(p-cumylbenzylsulfonyloxy) phenyl]-N'-[4-(p-cumylbenzylsulfonyloxy) phenyl] urea, N-[2-(p-cumylbenzenesulfonyloxy) phenyl]-N'-[4-(p-cumylbenzene sulfonyloxy) phenyl] urea, N-[2-(o-phenylbenzenesulfonyloxy) phenyl]-N'-[4-(o-phenyl) benzenesulfonyloxy phenyl] urea, N-[2-(p-phenylbenzenesulfonyloxy) phenyl]-N'-[4-(p-phenylbenzenesulfonyloxy) phenyl] urea, N-[2-(p-chlorobenzenesulfonyloxy) phenyl]-N'-[4-(p-chlorobenzene sulfonyloxy) phenyl] urea, N-[2-(ethanesulfonyloxy) phenyl]-N'-[4-(benzenesulfonyloxy) phenyl] urea, N-[2-(ethanesulfonyloxy) phenyl]-N'-[4-(p-toluenesulfonyloxy) phenyl] urea, N-[2-(benzenesulfonyloxy) phenyl]-N'-[4-(ethanesulfonyloxy) phenyl] urea, N-[2-(benzenesulfonyloxy) phenyl]-N'-[4-(benzylsulfonyloxy) phenyl] urea, N-[2-(benzenesulfonyloxy) phenyl]-N'-[4-(p-toluenesulfonyloxy) phenyl] urea, N-[2-(benzenesulfonyloxy) phenyl]-N'-[4-(o-toluenesulfonyloxy) phenyl] urea, N-[2-(benzenesulfonyloxy) phenyl-N'-[4-(p-ethylbenzenesulfonyloxy) phenyl] urea, N-[2-(benzenesulfonyloxy) phenyl]-N'-[4-(p-methoxybenzenesulfonyloxy) phenyl] urea, N-[2-(p-toluenesulfonyloxy) phenyl]-N'-[4-[benzenesulfonyloxy] phenyl] urea, N-[2-(p-toluenesulfonyloxy) phenyl]-N'-[4-(mesitylenesulfonyloxy) phenyl] urea, N-[2-(p-toluenesulfonyloxy) phenyl]-N'-[4-(1-naphthalenesulfonyloxy) phenyl] urea, N-[2-(benzylsulfonyloxy) phenyl]-N'-[4-(benzylsulfonyloxy) phenyl] urea, N-[2-(phenylethanesulfonyloxy) phenyl]-N'-[4-(phenylethanesulfonyloxy) phenyl] urea, N-[2-

(phenylpropanesulfonyloxy) phenyl]-N'-[4-(phenylpropanesulfonyloxy) phenyl] urea, N-[2-(p-methoxybenzylsulfonyloxy) phenyl]-N'-[4-(p-methoxybenzyl sulfonyloxy) phenyl] urea, N-[2-(ethanesulfonyloxy) phenyl]-N'-[4-(benzylsulfonyloxy) phenyl] urea, N-[2-(benzylsulfonyloxy) phenyl]-N'-[4-(methanesulfonyloxy) phenyl] urea, N-[2-(benzylsulfonyloxy) phenyl]-N'-[4-(butanesulfonyloxy) phenyl] urea, N-[2-(methanesulfonyloxy) phenyl]-N'-[4-(methanesulfonyloxy) phenyl] urea, N-[2-(ethanesulfonyloxy) phenyl]-N'-[4-(ethanesulfonyloxy) phenyl] urea, N-[2-(1-propanesulfonyloxy) phenyl]-N'-[4-(1-propanesulfonyloxy) phenyl] urea, N-[2-(2-propanesulfonyloxy) phenyl]-N'-[4-(2-propanesulfonyloxy) phenyl] urea, N-[2-(butanesulfonyloxy) phenyl]-N'-[4-(butanesulfonyloxy) phenyl] urea, N-[2-(pentanesulfonyloxy) phenyl]-N'-[4-(pentanesulfonyloxy) phenyl] urea, N-[2-(hexanesulfonyloxy) phenyl]-N'-[4-(hexanesulfonyloxy) phenyl] urea, N-[2-(cyclohexanesulfonyloxy) phenyl]-N'-[4-(cyclohexanesulfonyloxy) phenyl] urea, N-[2-(dodecanesulfonyloxy) phenyl]-N'-[4-(dodecanesulfonyloxy) phenyl] urea, N-[2-(methanesulfonyloxy) phenyl]-N'-[4-(propanesulfonyloxy) phenyl] urea, N-[2-(ethanesulfonyloxy) phenyl]-N'-[4-(propanesulfonyloxy) phenyl] urea, N-[2-(ethanesulfonyloxy) phenyl]-N'-[4-(butanesulfonyloxy) phenyl] urea, N-[2-(benzenesulfonyloxy) phenyl]-N'-[3-(benzenesulfonyloxy) phenyl] urea, N-[2-(p-toluenesulfonyloxy) phenyl]-N'-[3-(p-toluenesulfonyloxy) phenyl] urea, N-[2-(m-toluenesulfonyloxy) phenyl]-N'-[3-(m-toluenesulfonyloxy) phenyl] urea, N-[2-(o-toluenesulfonyloxy) phenyl]-N'-[3-(o-toluenesulfonyloxy) phenyl] urea, N-[2-(p-xylenesulfonyloxy) phenyl]-N'-[3-(p-xylenesulfonyloxy) phenyl] urea, N-[2-(m-xylenesulfonyloxy) phenyl]-N'-[3-(m-xylenesulfonyloxy) phenyl] urea, N-[2-(mesitylenesulfonyloxy) phenyl]-N'-[3-(mesitylenesulfonyloxy) phenyl] urea, N-[2-(1-naphthalenesulfonyloxy) phenyl]-N'-[3-(1-naphthalenesulfonyloxy) phenyl] urea, N-[2-(2-naphthalenesulfonyloxy) phenyl]-N'-[3-(2-naphthalene sulfonyloxy) phenyl] urea, N-[2-(p-ethylbenzenesulfonyloxy) phenyl]-N'-[3-(p-ethylbenzenesulfonyloxy) phenyl] urea, N-[2-(p-propylbenzenesulfonyloxy) phenyl]-N'-[3-(p-propylbenzene sulfonyloxy) phenyl] urea, N-[2-(p-isopropylbenzenesulfonyloxy) phenyl]-N'-[3-(p-isopropylbenzenesulfonyloxy) phenyl] urea, N-[2-(p-t-butylbenzenesulfonyloxy) phenyl]-N'-[3-(p-t-butylbenzenesulfonyloxy) phenyl] urea, N-[2-(p-methoxybenzenesulfonyloxy) phenyl]-N'-[3-(p-methoxybenzene sulfonyloxy) phenyl] urea, N-[2-(m-methoxybenzenesulfonyloxy) phenyl]-N'-[3-(m-methoxybenzenesulfonyloxy) phenyl] urea, N-[2-(o-methoxybenzenesulfonyloxy) phenyl]-N'-[3-(o-methoxybenzenesulfonyloxy) phenyl] urea, N-[2-(m,p-dimethoxy benzenesulfonyloxy) phenyl]-N'-[3-(m,p-dimethoxybenzenesulfonyloxy) phenyl] urea, N-[2-(p-ethoxybenzenesulfonyloxy) phenyl)-N'-[3-(p-ethoxybenzenesulfonyloxy) phenyl] urea, N-[2-(p-propoxybenzenesulfonyloxy) phenyl]-N'-[3-(p-propoxybenzene sulfonyloxy) phenyl] urea, N-[2-(p-butoxybenzenesulfonyloxy) phenyl]-N'-[3-(p-butoxybenzenesulfonyloxy) phenyl] urea, N-[2-(p-cumylbenzylsulfonyloxy) phenyl]-N'-[3-(p-cumylbenzylsulfonyloxy) phenyl] urea, N-[2-(p-cumylbenzenesulfonyloxy) phenyl]-N'-[3-(p-cumylbenzene sulfonyloxy) phenyl] urea, N-[2-(o-phenylbenzenesulfonyloxy) phenyl]-N'-[3-(o-phenylbenzenesulfonyloxy) phenyl] urea, N-[2-(p-phenylbenzenesulfonyloxy) phenyl]-N'-[3-(p-phenylbenzenesulfonyloxy) phenyl] urea, N-[2-(p-chlorobenzenesulfonyloxy) phenyl]-N'-[3-(p-chlorobenzene sulfonyloxy) phenyl] urea, N-[2-(ethanesulfonyloxy) phenyl]-N'-[3-(benzenesulfonyloxy) phenyl] urea, N-[2-(ethanesulfonyloxy) phenyl]-N'-[3-(p-toluenesulfonyloxy) phenyl] urea, N-[2-(benzenesulfonyloxy) phenyl]-N'-[3-(ethanesulfonyloxy) phenyl] urea, N-[2-(benzenesulfonyloxy) phenyl]-N'-[3-(benzylsulfonyloxy) phenyl] urea, N-[2-(benzenesulfonyloxy) phenyl]-N'-[3-(p-toluenesulfonyloxy) phenyl] urea, N-[2-(benzenesulfonyloxy) phenyl]-N'-[3-(o-toluenesulfonyloxy) phenyl] urea, N-[2-(benzenesulfonyloxy) phenyl]-N'-[3-(p-ethylbenzenesulfonyloxy) phenyl] urea, N-[2-(benzenesulfonyloxy) phenyl]-N'-[3-(p-methoxybenzenesulfonyloxy) phenyl] urea, N-[2-(p-toluenesulfonyloxy) phenyl]-N'-[3-(benzenesulfonyloxy) phenyl] urea, N-[2-(p-toluenesulfonyloxy) phenyl]-N'-[3-(mesitylenesulfonyloxy) phenyl] urea, N-[2-(p-toluenesulfonyloxy) phenyl]-N'-[3-(1-naphthalenesulfonyloxy) phenyl] urea, N-[2-(benzylsulfonyloxy) phenyl]-N'-[3-(benzylsulfonyloxy) phenyl] urea, N-[2-(phenylethanesulfonyloxy) phenyl]-N'-[3-(phenylethanesulfonyloxy) phenyl] urea, N-[2-(phenylpropanesulfonyloxy) phenyl]-N'-[3-(phenylpropanesulfonyloxy) phenyl] urea, N-[2-(p-methoxybenzylsulfonyloxy) phenyl]-N'-[3-(p-methoxybenzyl sulfonyloxy) phenyl] urea, N-[2-(ethanesulfonyloxy) phenyl]-N'-[3-(benzylsulfonyloxy) phenyl] urea, N-[2-(benzylsulfonyloxy) phenyl]-N'-[3-(methanesulfonyloxy) phenyl] urea, N-[2-(benzylsulfonyloxy) phenyl]-N'-[3-(butanesulfonyloxy) phenyl] urea, N-[2-(methanesulfonyloxy) phenyl]-N'-[3-(methanesulfonyloxy) phenyl] urea, N-[2-(ethanesulfonyloxy) phenyl]-N'-[3-(ethanesulfonyloxy) phenyl] urea, N-[2-(1-propanesulfonyloxy) phenyl]-N'-[3-(1-propanesulfonyloxy) phenyl] urea, N-[2-(2-propanesulfonyloxy) Phenyl]-N'-[3-(2-propanesulfonyloxy) phenyl] urea, N-[2-(butanesulfonyloxy) phenyl]-N'-[3-(butanesulfonyloxy) phenyl] urea, N-[2-(pentanesulfonyloxy) phenyl]-N'-[3-(pentanesulfonyloxy) phenyl] urea, N-[2-(hexanesulfonyloxy) phenyl]-N'-[3-(hexanesulfonyloxy) phenyl] urea, N-[2-(cyclohexanesulfonyloxy) phenyl]-N'-[3-(cyclohexanesulfonyloxy) phenyl] urea, N-[2-(dodecanesulfonyloxy) phenyl]-N'-[3-(dodecanesulfonyloxy) phenyl] urea, N-[2-(methanesulfonyloxy) phenyl]-N'-[3-(propanesulfonyloxy) phenyl] urea, N-[2-(ethanesulfonyloxy) phenyl]-N'-[3-(propanesulfonyloxy) phenyl] urea, N-[2-(ethanesulfonyloxy) phenyl]-N'-[3-(butanesulfonyloxy) phenyl] urea, and the like.

(Preparation Method of N,N'-Diarylurea Derivative)

The N,N'-diarylurea derivative of the present invention can be synthesized by reacting a compound represented by the general formula (4) with an aromatic amine compound represented by the general formula (5).

In addition, the N,N'-diarylurea derivative of the present invention can be synthesized by reacting a compound represented by the general formula (6) with an aromatic amine compound represented by the general formula (7).

For example, the N,N'-diarylurea derivative of the present invention can be synthesized by the following method.

(Synthesis Method)

Step 1.

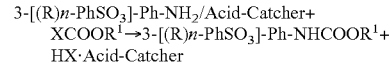

Step 2.

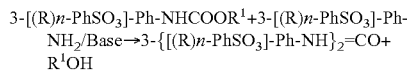

3-[(R)n-PhSO₃]-Ph-NHCOOR¹+3-[(R)n-PhSO₃]-Ph-NH₂/Base→3-{[(R)n-PhSO₃]-Ph-NH}₂=CO+ R¹OH (wherein $R^1$ represents an alkyl group or an aryl group, R represents an alkyl group, and n represents an integer of 0 to 3.)

$XCOOR^1$ used in Step 1 of the synthesis method mentioned above is a halogenated carbonic ester or carbonic diester, X is chloro, bromo, OMe, OEt, OPro or OPh, and $R^1$ is a Me, Et, Pro, or Ph group, or the like. In particular, methyl monochlorocarbonate, ethyl monochlorocarbonate, phenyl monochlorocarbonate, diethyl carbonate, and diphenyl carbonate are preferable.

The alkyl group for $R^1$ and R is the same as the alkyl group of the R mentioned above.

In the reaction, an organic base or an inorganic base is used as the acid-catcher, that is, the base.

As examples of the inorganic base, mention may be made of LiOH, NaOH, KOH, $NaHCO_3$, $KHCO_3$, $Na_2CO_3$, $K_2CO_3$, MeONa, EtONa, and the like.

As examples of the organic base, mention may be made of trimethylamine, triethylamine, tributylamine, pyridine, N,N-dimethylpyridine, 1,8-diazabicyclo [5,4,0] undecan-7-ene (DBU), and the like. Among these, $K_2CO_3$, triethylamine, pyridine, N,N-dimethylpyridine, and 1,8-diazabicyclo [5,4,0] undecan-7-ene (DBU) are preferable.

3-[(R)n-PhSO₃]-Ph-NH₂ can also be synthesized by directly subjecting 3-hydroxyaniline to O-sulfonation, or can be easily obtained by subjecting a nitrophenol compound to O-sulfonation, and subsequently reducing the nitro group.

As example of the 3-[(R)n-PhSO₃]-Ph-NH₂, mention may be made of 3-benzenesulfonyloxyaniline, 3-(p-toluene) sulfonyloxyaniline, 3-(m-toluene) sulfonyloxyaniline, 3-(o-toluene) sulfonyloxyaniline, 3-(p-xylene) sulfonyloxyaniline, 3-mesitylenesulfonyloxyaniline, and the like. Among these, 3-benzenesulfonyloxyaniline and 3-(p-toluene) sulfonyloxyaniline are preferable.

In general, an aprotic solvent can be used as the reaction solvent, and the reaction is carried out at a reaction temperature ranging from 0° C. to 180° C. In the present invention, the reaction is carried out at the temperature, for example, in the range of 0° C. to 180° C., and preferably in the range of 10° C. to 100° C. The solvent and reaction temperature are preferably selected in accordance with the boiling point of the solvent and the stability of the reaction product.

As examples of the aprotic solvent, mention may be made of aromatic hydrocarbons such as benzene, toluene, xylene, mesitylene, and the like, halogenated hydrocarbons such as dichloromethane, chloroform, dichloroethane, chlorobenzene, and the like, acetic esters such as ethyl acetate, propyl acetate, butyl acetate, phenyl acetate, benzyl acetate, and the like, ether compounds such as diethyl ether, dimethoxyethane, diethoxyethane, diethylene glycol dimethyl ether, dioxane, tetrahydrofuran, anisole, and the like, ketone compounds such as acetone, methyl ethyl ketone, methyl isobutyl ketone, and the like, acetonitrile, dimethyl sulfonamide, dimethyl sulfoxide, dimethyl imidazolidine, and the like.

In Step 2, 3-[(R)n-PhSO₃]-Ph-NHCOOR obtained in Step 1 and 3-[(R)n-PhSO₃]-Ph-NH₂ are reacted in the presence of a base.

The aforementioned reaction conditions used in Step 1 can be used for the base, reaction solvent, and reaction temperature in Step 2.

In addition, in order to simplify the reaction operation, Step 1 and Step 2 can be carried out simultaneously by using 2 or more equivalents of 3-[(R)n-PhSO₃]-Ph-NH₂.

In order to introduce urea groups, various methods for introducing urea groups have been proposed. For example, a method for forming urea groups from carbon monoxide introduction using a metal catalyst such as palladium or molybdenum, or carbonyl bisimidazole has been proposed. However, the catalyst and the reagent are expensive, and the operation is complicated. For this reason, such a method is not necessarily industrial.

The N,N'-diphenylurea derivatives represented by the aforementioned general formulae (1) to (3) of the present invention can also be synthesized by reacting the dihydroxydiphenylurea represented by the general formula (8) with a sulfonating agent represented by the formula (9) in the presence of an aprotic solvent. In particular, in the case of synthesizing a symmetrical compound, the preparation method of the present invention in which the dihydroxydiphenylurea is synthesized and then O-sulfonation is carried out is the most versatile and economical.

In addition, in accordance with the manufacturing method of the present invention, the step for producing the dihydroxydiphenylurea can be carried out in a smooth slurry state by selecting the reaction solvent. In addition, the next reaction can be carried out continuously without isolating the dihydroxydiphenylurea. The manufacturing method of the present invention has the industrial advantages described above.

The N,N'-diphenylurea derivatives represented by the general formulae (1) to (3) of the present invention can also be synthesized by reacting the aminophenol compound represented by the general formula (8-1) with urea in the presence of an aprotic solvent, and subsequently reacting with a sulfonating agent represented by the general formula (9). The step of producing the dihydroxydiphenylurea can smoothly proceed by means of the step of reacting the aminophenol compound represented by the general formula (8-1) with urea in the presence of an aprotic solvent, and therefore, the reaction can be carried out in a slurry state. In addition, the step of reacting with the sulfonating agent represented by the general formula (9) can be continuously carried out without isolating the dihydroxydiphenylurea.

The reaction of synthesizing the dihydroxydiphenylurea from the aminophenol and urea is carried out in an aprotic solvent at a reaction temperature ranging from 80° C. to 200° C. The reaction temperature preferably rages from 125 to 180° C.

As examples of the aminophenol, mention may be made of 2-aminophenol, 3-aminophenol, 4-aminophenol, 2-amino-5-methylphenol, 2-amino-4-methylphenol, 2-amino-6-methylphenol, 2-amino-4,5-dimethylphenol, 2-methyl-5-aminophenol, 3-methyl-5-aminophenol, 2,3-dimethyl-5-aminophenol, 2,4-dimethyl-5-aminophenol, 2,6-dimethyl-5-aminophenol, 3,4-dimethyl-5-aminophenol, 2-methyl-4-aminophenol, 3-methyl-4-aminophenol, 2,6-dimethyl-4-aminophenol, and the like.

As examples of the aprotic solvent, mention may be made of hydrocarbons such as tetralin, benzene, toluene, xylene, mesitylene, and the like, halogenated hydrocarbons such as trichloroethylene, chlorobenzene, dichlorobenzene, and the like, acetic esters such as ethyl acetate, propyl acetate, isobutyl acetate, butyl acetate, isoamyl acetate, amyl acetate, hexyl acetate, phenyl acetate, benzyl acetate, and the like, ether compounds such as diethoxyethane, diethylene glycol dimethyl ether, triethylene glycol dimethyl ether, dioxane, tetrahydrofuran, anisole, and the like, ketone compounds such as methyl ethyl ketone, methyl isobutyl ketone, diisobutyl ketone, acetophenone, benzophenone, and the like, tertiary amines such as tributylamine, pyridine, dimethylpyridine, diazabicycloundecene, and the like, aprotic polar solvents such as acetonitrile, benzonitrile, dimethylformamide, dimethyl sulfoxide, dimethyl imidazolidine, dimethylacetamide, and the like. The solvents mentioned above may be used in combinations of two or more types thereof.

As the preferred solvent, an aprotic water-insoluble solvent having a boiling point of 110° C. or higher is preferable, and an acetic ester having a boiling point that is the boiling point of butyl acetate or higher, or an aromatic hydrocarbon such as toluene or xylene is particularly preferable.

As examples of a treatment method after completion of the reaction, mention may be made of (1) a method in which the reaction liquid is cooled and filtered to isolate the dihydroxydiphenylurea, and then use it for the next reaction, and (2) a method in which the reaction liquid is cooled to the next reaction temperature, without isolating the dihydroxydiphenylurea, and the reaction liquid is provided to the next reaction as it is.

Next, the O-sulfonation reaction of the dihydroxydiphenylurea can be carried out by dropping a sulfonating agent into a reaction solution containing the dihydroxydiphenylurea, an acid-catcher, and an aprotic solvent. Alternatively, the reaction can be carried out by dropping an acid-catcher into a reaction solution composed of the dihydroxydiphenylurea, a sulfonating agent, and an aprotic solvent.

The reaction temperature of the O-sulfonation reaction may be in the range of 0° C. to 200° C. in the presence of an acid-catcher, and is preferably in the range of 10° C. to 150° C.

The O-sulfonation is carried out using a sulfonyl halide, or the like. As the sulfonyl halide, sulfonyl chloride is preferable. As examples thereof, mention may be made of ethanesulfonyl chloride, ethanesulfonyl chloride, n-propanesulfonyl chloride, i-propanesulfonyl chloride, butanesulfonyl chloride, benzylsulfonyl chloride, benzenesulfonyl chloride, p-toluenesulfonyl chloride, o-toluenesulfonyl chloride, p-xylenesulfonyl chloride, mesitylenesulfonyl chloride, p-ethylbenzenesulfonyl chloride, p-methoxybenzenesulfonyl chloride, p-chlorobenzenesulfonyl chloride, 1-naphthalenesulfonyl chloride, 2-naphthalenesulfonyl chloride, and the like.

As examples of the acid-catcher, mention may be made of organic bases such as trimethylamine, triethylamine, tributylamine, pyridine, dimethylaminopyridine, and the like, inorganic bases such as lithium hydroxide, sodium hydroxide, potassium hydroxide, calcium hydroxide, potassium hydrogen carbonate, sodium hydrogen carbonate, sodium carbonate, potassium carbonate, calcium carbonate, and the like, and bases such as sodium hydride, sodium methoxide, sodium ethoxide, and the like.

The solvent used in the O-sulfonation step of the dihydroxydiphenylurea is an aprotic solvent. As the aprotic solvent, acetic esters such as butyl acetate, isoamyl acetate, amyl acetate, hexyl acetate and the like, especially used in the previous step, the aromatic hydrocarbons such as toluene, xylene, mesitylene, and the like are particularly preferable. As the reaction solvent, the solvent used in the previous step may be used alone, or as a mixed solvent of two or more types thereof, or as a two-phase solvent system of water and a water-insoluble aprotic solvent.

When the reaction is carried out, the solvent and the reaction temperature can be suitably selected according to the reaction method in consideration of the boiling point of the solvent, the physical properties of the sulfonating agent, and the stability of the reaction product.

The reaction liquid after completion of the reaction is washed with water to remove the acid-catcher and the like.

In addition, in the case where a high purity is required, crystals may be washed or recrystallized by using aromatic hydrocarbons such as benzene, toluene, and the like, acetates such as ethyl acetate, isoamyl acetate, and the like, and alcohols such as methyl alcohol, ethyl alcohol, isopropyl alcohol, and the like.

(Thermo Sensitive Recording Material)

The thermosensitive recording material of the present invention is a thermosensitive recording material in which a thermosensitive recording layer containing a basic dye that is colorless or light-colored at room temperature and a color developer capable of coloring the basic dye by heating, provided on a base sheet, wherein the developer is the N,N'-diarylurea derivative mentioned above.

The thermosensitive recording layer of the thermosensitive recording material of the present invention can be formed by pulverizing into fine particles, and dispersing, for example, the basic dye mentioned above and the N,N'-diarylurea derivative represented by the general formula (1), general formula (2) or general formula (3), adding a binder, a sensitizer, a filler, a lubricant, and other various additives thereto to prepare a coating liquid, and applying the coating liquid on a base sheet such as paper, a plastic film, processed paper, or the like.

As examples of basic dyes which are colorless or light-colored at room temperature and used in the thermosensitive recording layer of the thermosensitive recording material according to the present invention, mention may be made of triphenylmethane-based compounds, fluoran-based compounds, diphenylmethane-based compounds, spiro-based compounds, fluorene-based compounds, and thiazine-based compounds, and it is possible to select from leuco dyes known in the related art.

For example, it is possible to select from 3,3-bis(p-dimethylamino phenyl)-6-dimethylamino phthalide, 3,3-bis (p-dimethylamino phenyl) phthalide, 3-(4-diethylamino-2-ethoxyphenyl)-3-(1-ethyl-2-methylindol-3-yl)-4-azaphthalide, 3,3-bis(P-methylamino phenyl)-6-dimethylamino phthalide, 3-diethylamino-7-dibenzylamino benzo[α]fluoran, 3-(1-ethyl-2-methylindol-3-yl)-3-(4-diethylamino-2-n-hexyloxyphenyl)-4-azaphthalide, 3-(1-ethyl-2-methylindol-3-yl)-3-(4-diethylamine)-2-methylphenyl-4-azaphthalide, 3-(4-diethylamino phenyl)-3-(1-ethyl-2-methylindol-3-yl) phthalide, 3-(2-methyl-1-n-octylindol-3-yl)-3-(4-diethylamino-2-ethoxyphenyl)-4-azaphthalide, 3-(N-ethyl-N-isopentylamino)-6-methyl-7-anilinofluoran, 3-diethylamino-6-methyl-7-anilinofluoran, 3-diethylamino-6-methyl-7-(o,p-dimethyl anilino) fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino) fluoran, 3-diethylamino-7-(m-trifluoromethylanilino) fluoran, 3-di(n-pentyl) amino-6-methyl-7-anilinofluoran, 3-[N-(3-ethoxypropyl)-N-ethylamino] 6-methyl-7-anilinofluoran, 3-(N,N-hexyl-N-ethylamino)-7-(o-chloroanilino) fluoran, 3-(N-ethyl-N-2-tetrahydrofurfurylamino)-6-methyl-7-anilinofluoran, 2,2-bis{4-[6'-(N-cyclohexyl-N-methylamino)-3'-methylspiro [phthalide-3,9'-xanthen]-2'-ylamino]phenyl}propane, and 3-dibutylamino-7-(o-chloroanilino) fluoran, 3,6-dimethoxyfluorane, 3-pyrrolidino-6-chlorofluoran, 3-diethylamino-6-methyl-7-chlorofluoran, 3-diethylamino-7-chlorofluoran, 3-diethylamino-7,8-dibenzofluoran, 3-diethylamino-6,7-dimethyl fluoran, 3-(N-methyl-p-toluidino)-7-methyl fluoran, 3-(N-methyl-N-isoamylamino)-7,8-benzofluoran, 3,3'-bis(1-n-amyl-2-methylindol-3-yl) phthalide, 3-(N-methyl-N-isoamylamino)-7-phenoxyfluoran, 3,3'-bis(1-n-butyl-2-methylindol-3-yl) phthalide, 3,3'-bis(1-ethyl-2-methylindol-3-yl) phthalide, 3,3'-bis(p-dimethylamino phenyl) phthalide, 3-(N-ethyl-N-p-tolylamino)-7-(N-phenyl-N-methylamino) fluoran, 3-diethylamino-7-anilinofluoran, 3-diethylamino-7-benzylaminofluoran, 3-pyrrolidino-7-dibenzylaminofluoran, and the like. However, the basic dyes of the present invention are not limited thereto, and two or more types thereof may be used together.

In the thermosensitive recording layer of the thermosensitive recording material of the present invention, a sensitizer can be used as necessary, and a conventionally known sensitizer can be used as the sensitizer.

As examples thereof, mention may be made of, for example, fatty acid amides such as stearic acid amide, bisstearic acid amide, palmitic acid amide, and the like, p-toluenesulfonamide, fatty acid metal salts such as calcium, zinc or aluminum salts of fatty acids such as stearic acid, behenic acid, palmitic acid, and the like, p-benzylbiphenyl, diphenylsulfone, benzyl benzyloxybenzoate, 2-benzyloxynaphthalene, 1,2-bis (p-tolyloxy) ethane, 1,2-bis (phenoxy) ethane, 1,2-bis (3-methylphenoxy) ethane, 1,3-bis (phenoxy) propane, dibenzyl oxalate, p-methylbenzyl oxalate, m-terphenyl, 1-hydroxy-2-naphthoic acid, and the like.

In particular, 1,2-bis (p-tolyloxy) ethane and 1,2-bis (phenoxy) ethane are preferable in view of sensitivity.

In addition, it is possible to use a storage stabilizer known in the related art in the thermosensitive recording layer of the thermosensitive recording material of the present invention.

As examples thereof, mention may be made of, for example, hindered phenol compounds such as 2,2'-methylene bis (4-methyl-6-tert-butylphenol), 2,2'-methylene bis (4-ethyl-6-tert-butylphenol), 2,2'-ethylidene bis (4,6-di-tert-butylphenol), 4,4'-thio bis (2-methyl-6-tert-butylphenol), 4,4'-butylidene bis (6-tert-butyl m-cresol), 1,1,3-tris (2-methyl-4-hydroxy-5-tert-butylphenyl) butane, 1,1,3-tris (2-methyl-4-hydroxy-5-cyclohexylphenyl) butane, 4,4'-bis [(4-methyl-3-phenoxycarbonylamino phenyl) ureido] diphenylsulfone, tris (2,6-dimethyl-4-tert-butyl-3-hydroxybenzyl) isocyanurate, 4,4'-thio bis (3-methylphenol), 4,4'-dihydroxy-3,3',5,5'-tetrabromodiphenylsulfone, 4,4'-dihydroxy 3,3',5,5'-tetramethyldiphenylsulfone, 2,2-bis (4-hydroxy-3,5-dibromophenyl) propane, 2,2-bis (4-hydroxy-3,5-dichlorophenyl) propane, 2,2-bis (4-hydroxy-3,5-dimethyl phenyl) propane, and the like, epoxy compounds such as 1,4-diglycidyloxy benzene, 4,4'-diglycidyloxy diphenylsulfone, 4-benzyloxy-4'-(2-methylglycyloxy) diphenylsulfone, glycidyl terephthalate, bisphenol A type epoxy resin, cresol novolac type epoxy resin, phenol novolac type epoxy resin, and the like, N,N'-di-2-naphthyl-p-phenylene diamine, a sodium salt or a polyvalent metal salt of 2,2'-methylene bis (4,6-di-tert-butylphenyl) phosphate, bis (4-ethyleneimine carbonylamino phenyl) methane, and a diphenylsulfone cross-linking type compound represented by the following general formula (10), and the like.

In particular, 1,1,3-tris (2-methyl-4-hydroxy-5-tert-butylphenyl) butane, 1,1,3-tris (2-methyl-4-hydroxy-5-cyclohexylphenyl) butane, 4,4'-bis [(4-methyl-3-phenoxycarbonylamino phenyl) ureido] diphenylsulfone, and a diphenylsulfone cross-linking type compound represented by the following general formula (10) are suitable for further improving the storage stability.

[Chem. 12]

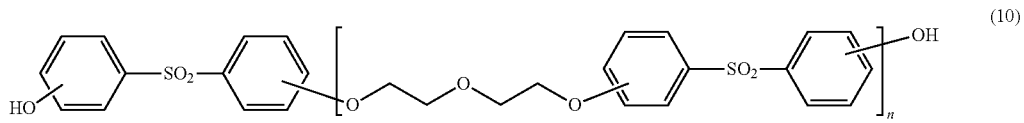

(10)

(In the formula, n represents an integer ranging from 1 to 7.)

In addition, in the thermosensitive recording layer of the thermosensitive recording material of the present invention, an auxiliary agent can be used as necessary. As examples of the auxiliary agents, mention may be made of, for example, dispersants such as sodium dioctyl succinate, sodium dodecylbenzene sulfonate, sodium lauryl alcohol sulfate, fatty acid metal salts, and the like, zinc stearate, calcium stearate and higher fatty acid metal salts, higher fatty acid amides such as stearic acid amide, and the like, waxes such as paraffin, polyethylene wax, oxidized polyethylene wax, caster wax, ester wax, and the like, hydrazide compounds such as adipic acid dihydrazide, and the like, water-resistant agents such as glyoxal, boric acid, dialdehyde starch, methylol urea, glyoxylate, epoxy compounds, and the like, antifoaming agents, coloring dyes, fluorescent dyes, and pigments, and the like.

As examples of the binder used in the thermosensitive recording layer of the present invention, mention may be made of starches such as oxidized starch, esterified starch, etherified starch, and the like, celluloses such as methylcellulose, carboxymethylcellulose, methoxycellulose, hydroxyethylcellulose, and the like, casein, gelatin, polyvinyl alcohols such as complete (or partially) saponified polyvinyl alcohol, carboxy-modified polyvinyl alcohol, acetoacetyl-modified polyvinyl alcohol, silicon-modified polyvinyl alcohol, amide-modified polyvinyl alcohol, sulfonic acid-modified polyvinyl alcohol, butyral-modified polyvinyl alcohol, and the like, styrene-maleic anhydride copolymer, styrene-butadiene copolymer resin, vinyl acetate resin, urethane resin, acrylamide resin, acrylate resin, vinyl butyral-styrol, and copolymer resins thereof, amide resin, silicone resin, petroleum resin, terpene resin, ketone resin, chroman resin, and the like. These binders can be used alone or in combination of two or more types. The binders may be used by dissolving in a solvent, or may be used in a state of being emulsified or dispersed as a paste in water or another medium.

As examples of the pigments to be blended in the thermosensitive recording layer, mention may be made of inorganic or organic pigments such as amorphous silica, amorphous calcium silicate, heavy calcium carbonate, light calcium carbonate, kaolin, calcined kaolin, diatomaceous earth, talc, titanium dioxide, zinc oxide, aluminum hydroxide, magnesium hydroxide, barium sulfate, colloidal silica, polystyrene powder, nylon powder, urea-formalin resin filler, styrene-methacrylic acid copolymer, styrene-butadiene copolymer, hollow plastic pigment, and the like.

The types and usage amounts of the additives such as basic dyes, color developers, sensitizers, binders, pigments and other auxiliary agents, used in the thermosensitive recording layer in the present invention can be suitably determined according to the quality performance required for the thermosensitive recording layer.

In the thermosensitive recording layer in the present invention, the content of the N,N'-diarylurea derivative represented by the aforementioned general formula (1) as a developer preferably ranges from 0.3 to 5 parts by mass, and more preferably ranges from 0.4 to 3 parts by mass with respect to one part by mass of the basic dye in the thermosensitive recording layer from the viewpoint of color density.

In addition, the sensitizer is suitably contained in an amount ranging from 0.2 to 4 parts by mass with respect to 1 part of the leuco dye, and the binder is suitably contained in an amount ranging from 5 to 50% by mass in the total solid content. As the base sheet, paper, recycled paper, synthetic paper, a plastic film, nonwoven fabric, metal foil or the like can be used. In addition, a hybrid sheet combining these can also be used.

In addition, an overcoating layer formed from a polymer substance containing an organic pigment may be provided for the purpose of improving preservability. In addition, an undercoat layer containing an organic pigment, an inorganic pigment, hollow fine particles, expanded particles, and the like may be provided for the purpose of preventing scum adhesion to the thermal head, improving the print image quality, and improving sensitivity.

The basic dye, the developer, the sensitizer, and if necessary, the storage stabilizer and the like, used for the thermosensitive recording layer in the present invention are finely dispersed by means of a stirring pulverizer such as a ball mill, an attritor, a sand mill, or the like, using for example, water as a dispersion medium so that the particle diameter is 2 μm or less, and then used.

A coating material for the thermosensitive recording layer can be prepared by mixing and stirring the dispersion finely dispersed as described above, with pigments, binders, auxiliary agents, and the like as necessary.

The thermosensitive layer can be formed by applying the coating material for the thermosensitive recording layer obtained as described above on the base sheet so that a coating amount after being dried ranges from about 1.0 to 20 g/m$^2$, preferably ranges from about 1.5 to 12 g/m$^2$, more preferably ranges from about 2.0 to 7.0 g/m$^2$, and particularly preferably ranges from about 3 to 7 g/m$^2$, and then by drying.

The coating method for forming the thermosensitive layer is not particularly limited. For example, coating can be carried out by means of an appropriate coating method such as air knife coating, barrier coating, pure blade coating, rod blade coating, curtain coating, die coating, slide velvet coating, offset gravure coating, five-roller coating, or the like.

The thermosensitive recording layer may be laminated on the base sheet by directly applying the coating material for the thermosensitive recording layer prepared as described above to the base sheet. Alternatively, an undercoat layer is first formed on the base sheet, and then the thermosensitive recording layer may be formed on the formed undercoat layer. By providing the undercoat layer, it is possible to improve sensitivity and image quality, as well as improve a printing scum absorption function.

The composition of the undercoat layer may be appropriately selected depending on the purpose, but generally includes a binder, a pigment, and the like.

As the binder used for the undercoat layer, a resin used in the thermosensitive recording layer can be used. That is, starches such as oxidized starch, esterified starch, etherified starch, and the like, cellulose resins such as methylcellulose, carboxycellulose, methoxycellulose, methoxycellulose, hydroxyethylcellulose, and the like, casein, gelatin, polyvinyl alcohols such as fully (or partially) saponified polyvinyl alcohol, carboxy-modified polyvinyl alcohol, acetoacetyl-modified polyvinyl alcohol, silicon-modified polyvinyl alcohol, amide-modified polyvinyl alcohol, sulfonic acid-modified polyvinyl alcohol, butyral-modified polyvinyl alcohol, and the like, styrene-maleic anhydride copolymer latex, styrene-butadiene copolymer latex, vinyl acetate resin latex, urethane resin latex, acrylic resin latex, and the like, can be used.

As examples of the inorganic pigments contained in the undercoat layer, mention may be made of metal compounds such as a metal oxide, a metal hydroxide, a sulfuric acid salt and a carbonic acid salts, such as aluminum hydroxide, magnesium hydroxide, barium sulfate, aluminum silicate, calcium carbonate, and the like, and inorganic white pigments such as amorphous silica, calcined kaolin, talc, and the like. Among these, in particular, calcined kaolin is preferably used due to superior color development sensitivity, superior sensitivity and superior scum absorption. The particle diameter of the inorganic pigment preferably ranges from about 0.5 to 3.0 μm.

In addition, as examples of organic pigments contained in the undercoat layer, mention may be made of spherical resin particles (so-called dense resin particles), hollow particles, resin particles having through-holes, reins having an opening portion which can be obtained by cutting a part of the hollow resin particles on the surface, and the like. In order to enhance recording density, hollow resins are preferably used.

In order to achieve both the sensitivity and the scum adhesion, an inorganic pigment system and an organic resin system are commonly used in combination, and the usage ratio of the inorganic pigment to the organic pigment ranges from about 90:10 to 30:70, and more preferably ranges from 70:30 to 50:50, by mass ratio.

In addition, in order to improve the sensitivity, a foamed resin can also be used.

The undercoat layer is generally formed by applying an undercoat material obtained by mixing and stirring at least one type of pigment selected from inorganic pigments and organic pigments and a binder with water as a dispersion medium, on a base sheet, and then drying so that the application amount after drying on the base sheet ranges from about 1 to 20 g/m$^2$ and preferably ranges from about 5 to 15 g/m$^2$. The usage amount of the binder mentioned above ranges from about 5 to 40% by mass and the usage amount of the pigments mentioned above ranges from about 10 to 95% by mass, with respect to the total solid content of the undercoat layer. In addition, various auxiliary agents such as lubricants fluorescent dyes, coloring dyes, surfactants, cross-linking agents, and the like, such as zinc stearate, calcium stearate, paraffin wax, and the like, may be added to the coating material for the undercoat layer, as necessary.

The undercoat layer may be a single layer, or in some cases, two or more layers may be provided therefor.

A protective layer mainly composed of a binder having a film-forming property may be provided on the thermosensitive recording layer. The coating material for the protective layer is prepared by, for example, using water as a medium, and mixing and stirring a binder component and a pigment as well as an auxiliary agent, if necessary.

As the binder, pigment and auxiliary agent used in the protective layer, those used in the thermosensitive recording layer mentioned above can be used.

In addition, a glossy layer may be provided on the protective layer. The glossy layer may be provided, for example, by a method in which a coating liquid having an electron beam curable compound or an ultraviolet curable compound as a main component is applied, and subsequently an electron beam or ultraviolet ray is irradiated to cure the compound, a method in which an ultrafine core-shell type acrylic resin is used, or the like. In addition, an antistatic layer may be provided on the back side of the base sheet.

The coating material for forming the undercoat layer, the protective layer, the glossy layer, or the like can be applied by means of an appropriate application method such as pure blade coating, rod blade coating, curtain coating, offset gravure coating, or the like, in the same manner as that of the thermosensitive recording layer, and then drying is carried out, and thereby, each of the layers can be formed.

After each of the layers is formed, various known processing techniques in the field of manufacturing of the thermosensitive recording material such as a super calendaring treatment may be added as appropriate.

EXAMPLES

Hereinafter, the present invention is described in detail with reference to Examples and Comparative Examples. However, it should be understood that the present invention is not limited thereto. In the Examples, "parts" and "%" respectively indicate "parts by mass" and "% by mass".

Measurement of the melting point can be carried out at a heating rate of 1° C./min using a device for the measurement of a melting point (manufactured by Buchi AG).

Synthesis Examples of N,N'-diphenylurea derivatives are shown below. Thermal analysis was measured with a differential thermal analyzer (DSC 60 manufactured by Shimadzu Corporation). The measurement was carried out under a nitrogen stream at a heating rate of 10° C./min, and the endothermic temperature (melting point) was measured.

Synthesis Example 1

Synthesis of N,N'-di-[3-(p-toluenesulfonyloxy) phenyl] urea 5.26 g of 3-(p-toluenesulfonyloxy) aniline and 2.20 g of triethylamine were dissolved in ethyl acetate in a four-necked flask equipped with a thermometer, a stirrer, and a dropping funnel, and the internal temperature was adjusted to 20° C. While controlling the internal temperature at 20° C. under a nitrogen atmosphere, 3.29 g of phenyl chlorocarbonate was added dropwise, and the mixture was stirred for 4 hours and allowed to stand for 1 day. Water was added to the reaction solution, the organic layer was washed with water, and anhydrous MgSO$_4$ was added to the organic layer to dry the organic layer. The solvent was distilled off under reduced pressure using an evaporator to obtain a concentrated residue of N-phenoxycarbonyl-3-(p-toluenesulfonyloxy) aniline, which was subsequently dissolved in dioxane.

Subsequently, 5.26 g of 3-(p-toluenesulfonyloxy) aniline, DBU, and dioxane were added to a four-necked flask, and the mixture was heated to 100° C. To the aforementioned dioxane solution, a dioxane solution in which the concentrated residue of N-phenoxycarbonyl-3-(p-toluenesulfonyloxy) aniline was dissolved in dioxane was added dropwise while maintaining the internal temperature of the dioxane solution of the concentrated residue of N-phenoxycarbonyl-3-(p-toluenesulfonyloxy) aniline. The reaction was carried out for 7 hours. The internal temperature was cooled to 40° C., and ethyl acetate was added to the reaction solution. The organic layer was washed with a diluted hydrochloric acid, an aqueous solution of sodium hydrogen carbonate, and water. The organic layer was dried over anhydrous MgSO$_4$, and subsequently, the solvent was distilled off. MeOH was added to the concentrated residue to precipitate crystals.

The crystals were separated by filtration to obtain 8.6 g of pale brown crystals of N,N'-di-[3-(p-toluenesulfonyloxy) phenyl] urea. Melting point: 164° C. to 168° C. An IR chart is shown in FIG. 1.

Synthesis Example 2

Synthesis of N,N'-di-[3-(p-toluenesulfonyloxy) phenyl] urea 10.9 g of 3-aminophenol, 3.03 g of urea and 40 g of isoamyl acetate were placed in a four-necked flask equipped with a thermometer, a stirrer, and a nitrogen introducing tube. The mixture was heated under a nitrogen atmosphere. The mixture was stirred at 125° C. for 2 hours, and further heated to 135° C. to continue the reaction. During the reaction, crystals were precipitated, but the stirring was continued to carry out the reaction for 10 hours as it was. After completion of the reaction, the reaction solution was cooled to 10° C., and the precipitated crystals were separated by filtration and dried under reduced pressure. Thereby, 11.8 g of crystals of 3,3'-dihydroxydiphenylurea were obtained. Subsequently, a four-necked flask equipped with a thermometer, a stirrer, and a nitrogen introducing tube was charged with 11.8 g of 3,3'-dihydroxydiphenylurea, 18.5 g (97.0 mM) of p-toluenesulfonyl chloride, and 80 g of ethyl acetate, and the atmosphere was replaced with nitrogen. After the internal temperature of the flask was set to 70° C., 11.1 g of triethylamine was added dropwise thereto, while the internal temperature was maintained at 70° C. The mixture was stirred and reacted for 4 hours at 70° C., and then cooled to 50° C. An aqueous solution of hydrochloric acid was added thereto to separate off an aqueous layer. An organic layer was concentrated, and methyl alcohol was added to the concentrated residue for crystallization. The crystals were obtained by filtration and dried under reduced pressure. Thereby, 25.8 g of N,N'-di-[3-(p-toluenesulfonyloxy) phenyl] urea was obtained. Melting point: 166° C. to 169° C.

Figure 2:
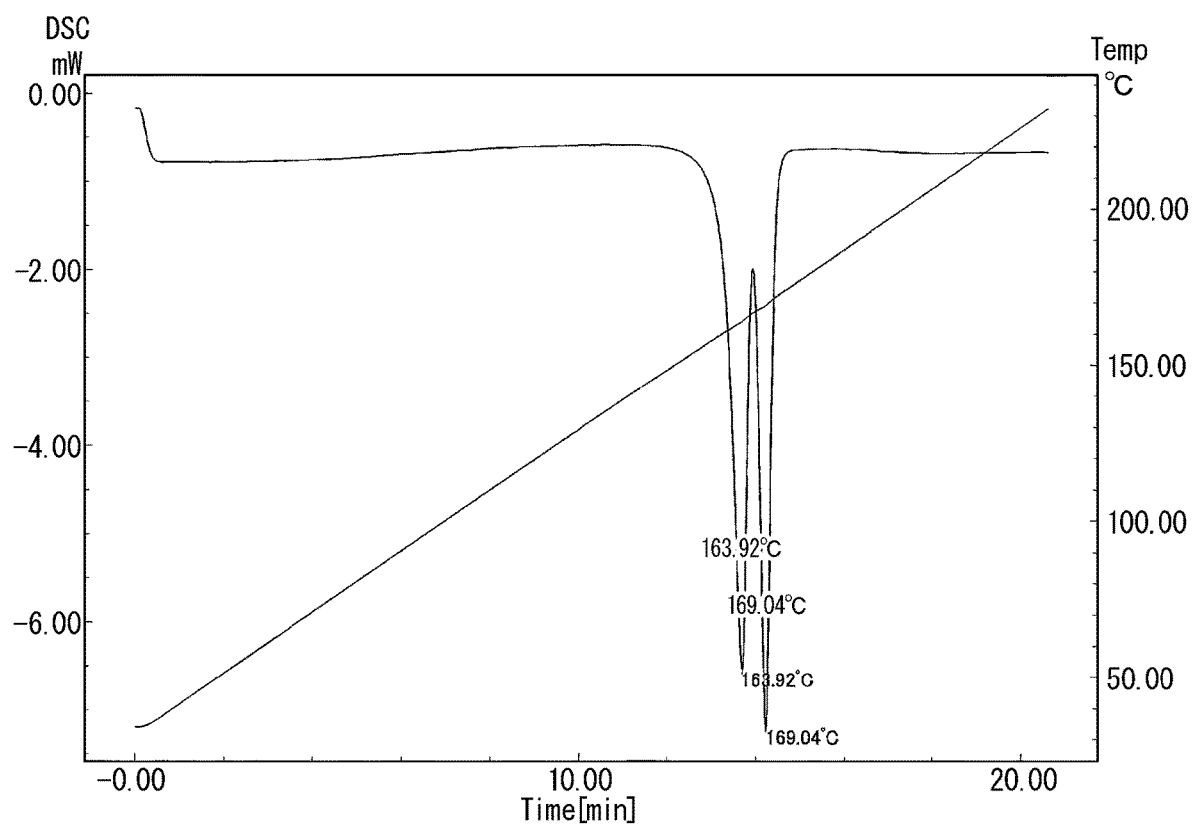
FIG. 2 shows a DSC chart of N,N'-di-[3-(p-toluenesulfonyloxy) phenyl] urea (Sample 1 of Synthesis Example 2) according to the present invention.
Figure 3:
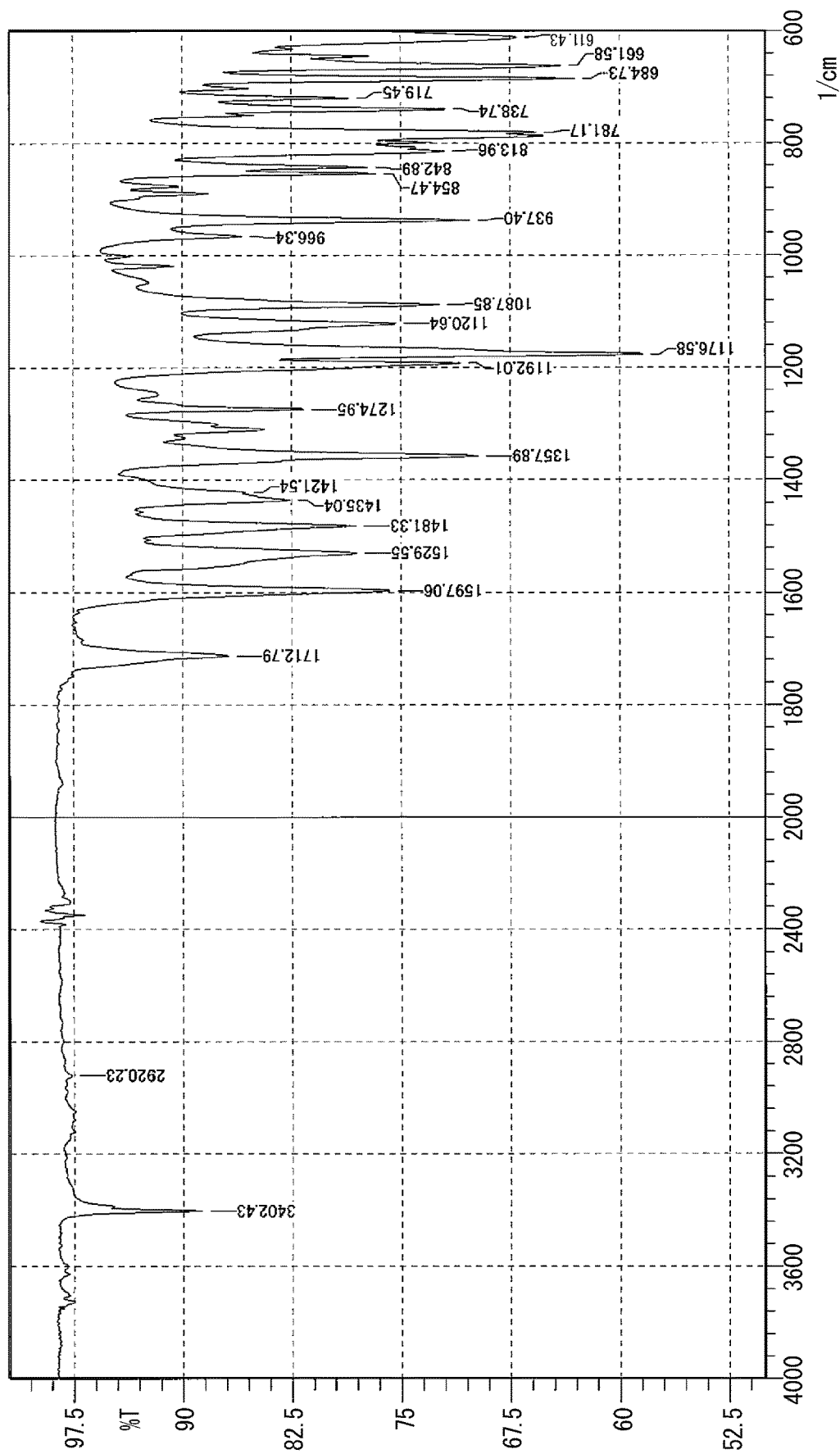
FIG. 3 shows an IR chart of N,N'-di-[3-(p-toluenesulfonyloxy) phenyl] urea (Sample 1 of Synthesis Example 2) according to the present invention.

It can be seen that the crystals obtained in Synthesis Example 2 indicates two peak tops at 164° C. and 169° C. according to thermal analysis (refer to the DSC chart in FIG. 2 (Sample 1)). An IR chart of N,N'-di-[3-(p-toluenesulfonyloxy) phenyl] urea of Sample 1 obtained in Synthesis Example 2 is shown in FIG. 3.

Next, acetonitrile was added to the crystals mentioned above, and filtration thereof while being hot was carried out.

Figure 4:
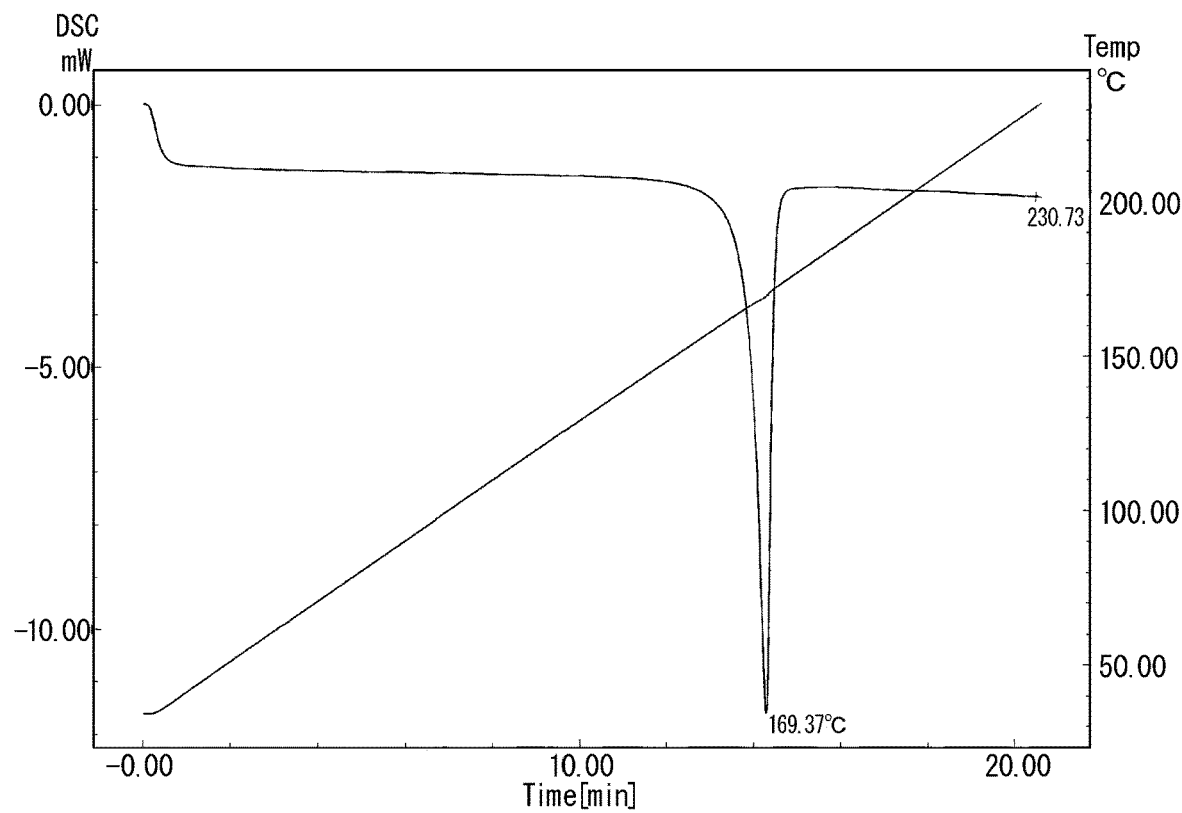
FIG. 4 shows a DSC chart of N,N'-di-[3-(p-toluenesulfonyloxy) phenyl] urea (Sample 2 of Synthesis Example 2) according to the present invention.

It can be seen that the obtained crystals indicate one peak top at 169° C. according to thermal analysis (refer to the DSC chart in FIG. 4 (Sample 2)).

Figure 5:
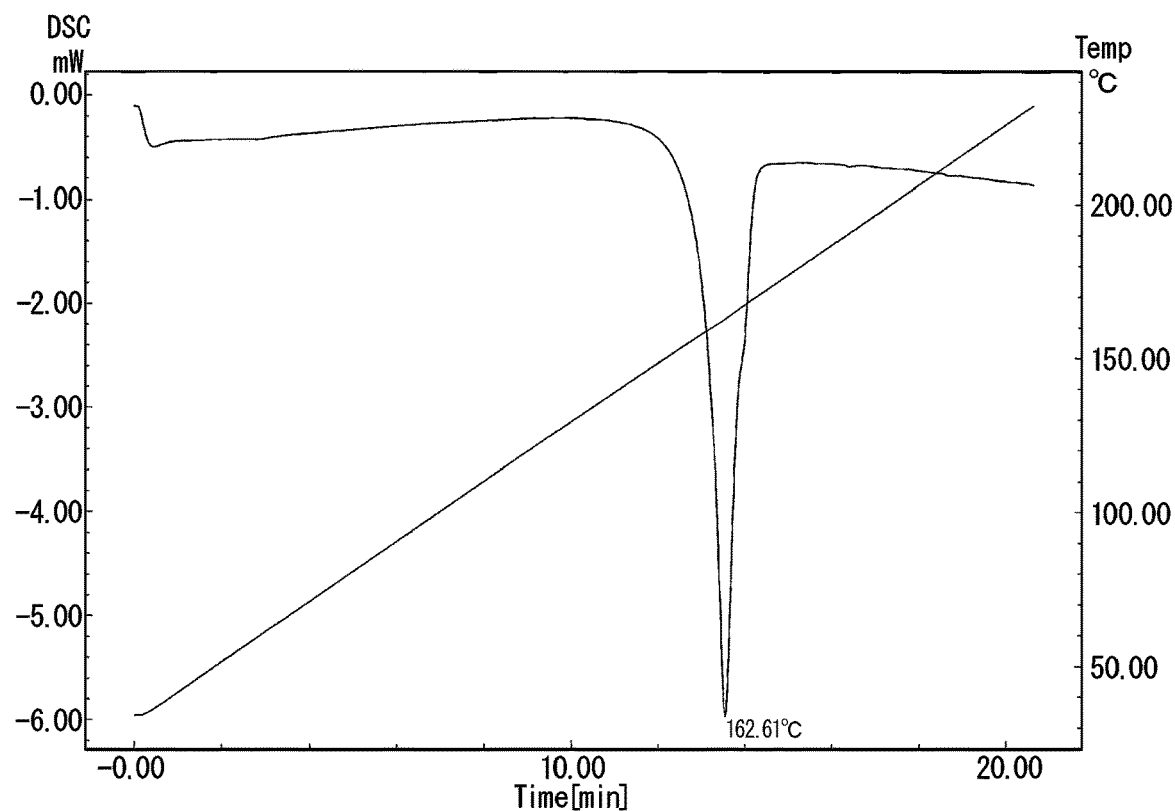
FIG. 5 shows a DSC chart of N,N'-di-[3-(p-toluenesulfonyloxy) phenyl] urea (Sample 3 of Synthesis Example 2) according to the present invention.

In addition, the filtrate was cooled and the crystals were taken out. It can be seen that the obtained crystals indicate one peak top at 163° C. according to thermal analysis (refer to the DSC chart in FIG. 5 (Sample 3)).

Synthesis Example 3

Synthesis of N,N'-di-[3-(p-toluenesulfonyloxy) phenyl] urea

The same operations as those described in Synthesis Example 2 were carried out, and the reaction was carried out for 10 hours at 137° C. Subsequently, the internal temperature was cooled to 75° C. Without separating the precipitated crystals, 19.0 g of p-toluenesulfonyl chloride was added to the slurry, and 12.0 g of triethylamine was added dropwise to the reaction solution while maintaining the internal temperature. The reaction was carried out for 5 hours. After completion of the reaction, water was added, and neutralization was carried out with acetic acid so that crystals were precipitated. The internal temperature was cooled to 10° C., and the crystals were separated by filtration. Subsequently, the wet crystals were washed with water and methyl alcohol and dried under reduced pressure. Thereby, 25.6 g of N,N'-di-[3-(p-toluenesulfonyloxy) phenyl] urea was obtained.

Melting point: 166° C. to 169° C.

The crystals indicated two peak tops at 164° C. and 169° C. according to thermal analysis in the same manner as described in Sample 1.

Synthesis Example 4

Synthesis method of N,N'-di-[3-(p-toluenesulfonyloxy) phenyl] urea (Two-Phase Reaction)

The same operations as those described in Synthesis Example 2 were carried out, and the reaction was carried out for 10 hours at 137° C. Subsequently, the internal temperature was cooled to 40° C. 10.5 g of 40% sodium hydroxide was added to the aforementioned reaction solution at 40° C. to dissolve 3,3'-dihydroxydiphenylurea. A solution of p-toluenesulfonyl chloride dissolved in isoamyl acetate was added dropwise to the solution mentioned above, and reacted for 8 hours. After completion of the reaction, the reaction mixture was neutralized with acetic acid and cooled, and the crystals were filtered. Subsequently, the crystals separated by filtration were washed with water and methyl alcohol and then dried. Thereby, 25.4 g of N,N'-di-[3-(p-toluenesulfonyloxy) phenyl] urea was obtained. Melting point: 166° C. to 169° C.

The crystals indicated two peak tops at 164° C. and 169° C. according to thermal analysis in the same manner as described in Sample 1.

Synthesis Example 5

Synthesis of N,N'-di-3-(p-toluenesulfonyloxy) phenyl] urea

A four-necked flask was charged with 12.2 g of 3,3'-dihydroxydiphenylurea obtained by the same operations as those described in Synthesis Example 2, 20.0 g of p-toluenesulfonyl chloride, and isoamyl acetate. 100 g of a 4.2% aqueous solution of sodium hydroxide was added dropwise thereto, while maintaining the internal temperature at 65 to 75° C., and the reaction was continued for 4 hours. After completion of the reaction, the reaction mixture was neutralized with dilute hydrochloric acid and cooled. The precipitated crystals were separated by filtration. The separated crystals were washed with methyl alcohol and then dried under reduced pressure. Thereby, 25.8 g of N,N'-di-3-(p-toluenesulfonyloxy) phenyl] urea was obtained.

Melting point: 158° C. to 161° C.

Figure 6:
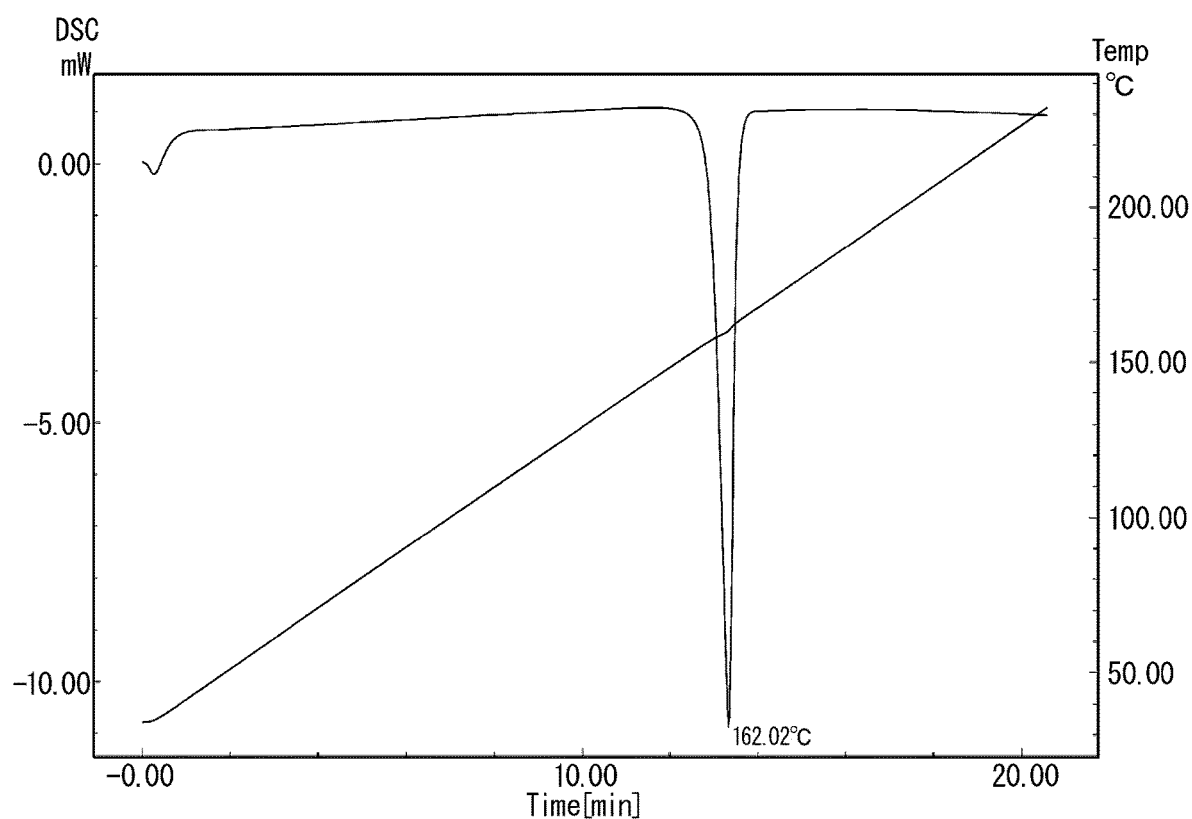
FIG. 6 shows a DSC chart of N,N'-di-[3-(p-toluenesulfonyloxy) phenyl] urea (Synthesis Example 5) according to the present invention.
Figure 7:
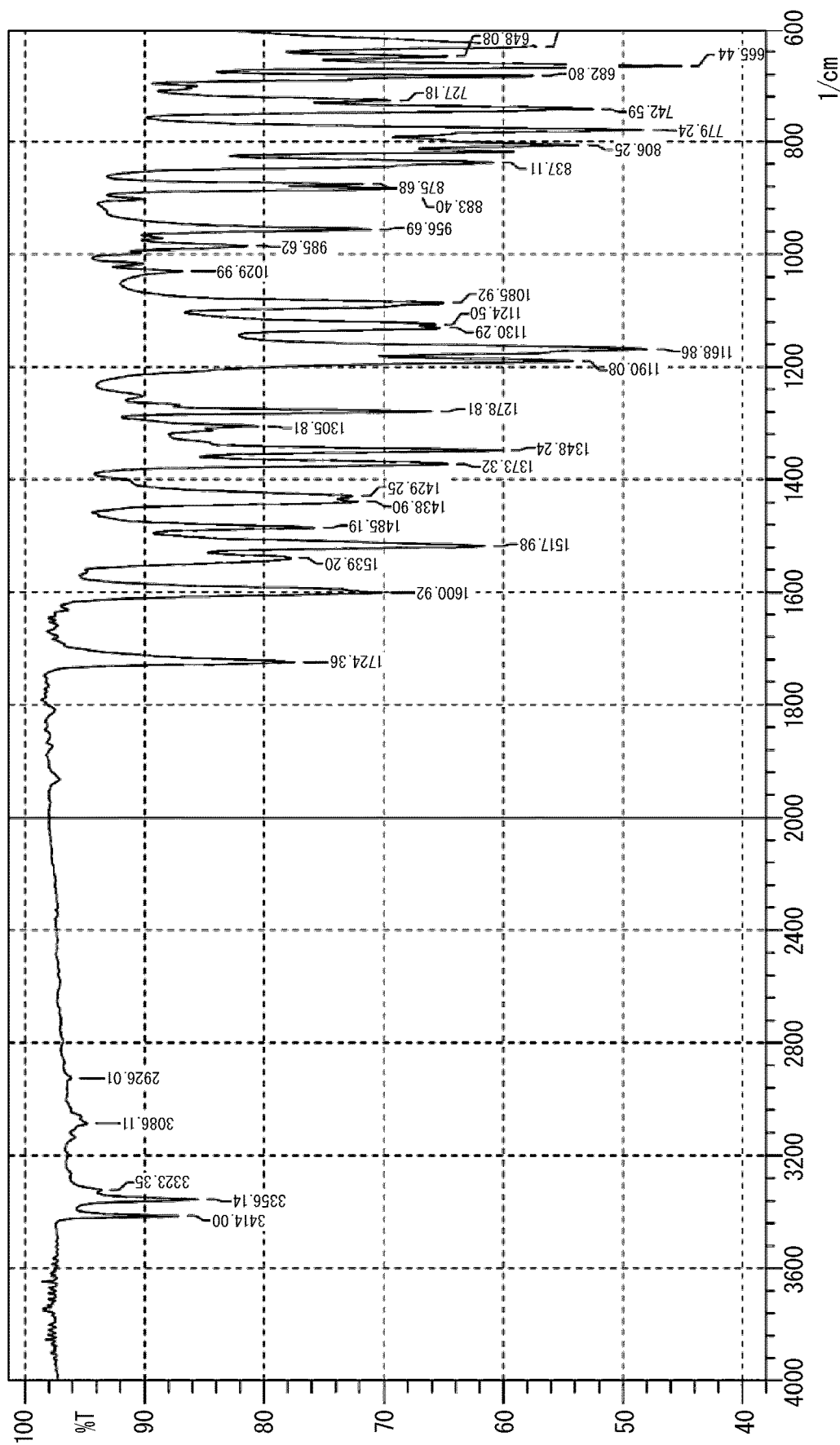
FIG. 7 shows an IR chart of N,N'-di-[3-(p-toluenesulfonyloxy) phenyl] urea (Synthesis Example 5) according to the present invention.

The crystals indicated one peak top at 160° C. according to thermal analysis (refer to the DSC chart in FIG. 6). An IR chart of N,N'-di-[3-(p-toluenesulfonyloxy) phenyl] urea of Sample 1 obtained in Synthesis Example 5 is shown in FIG. 7.

Synthesis Example 6

Synthesis of N,N'-di-[3-(o-toluenesulfonyloxy) phenyl] urea

The same operations as those described in Synthesis Example 2 were carried out, with the exception of replacing p-toluenesulfonyl chloride used in Synthesis Example 2 with o-toluenesulfonyl chloride, to obtain a concentrated residue. Subsequently, ethyl alcohol was added to the concentrated residue for crystallization, and filtration was carried out. Thereby, crystals were obtained.

Melting point: 140° C. to 142° C.

Synthesis Example 7

Synthesis of N,N'-di-[3-(benzenesulfonyloxy) phenyl] urea

The same operations as those of Synthesis Example 1 were carried out, with the exception of replacing 5.26 g of 3-(p-toluenesulfonyloxy) aniline of Synthesis Example 1 with 4.98 g of 3-(benzenesulfonyloxy) aniline. Thereby, N,N'-di-[3-(benzenesulfonyloxy) phenyl] urea was synthesized.

Figure 8:
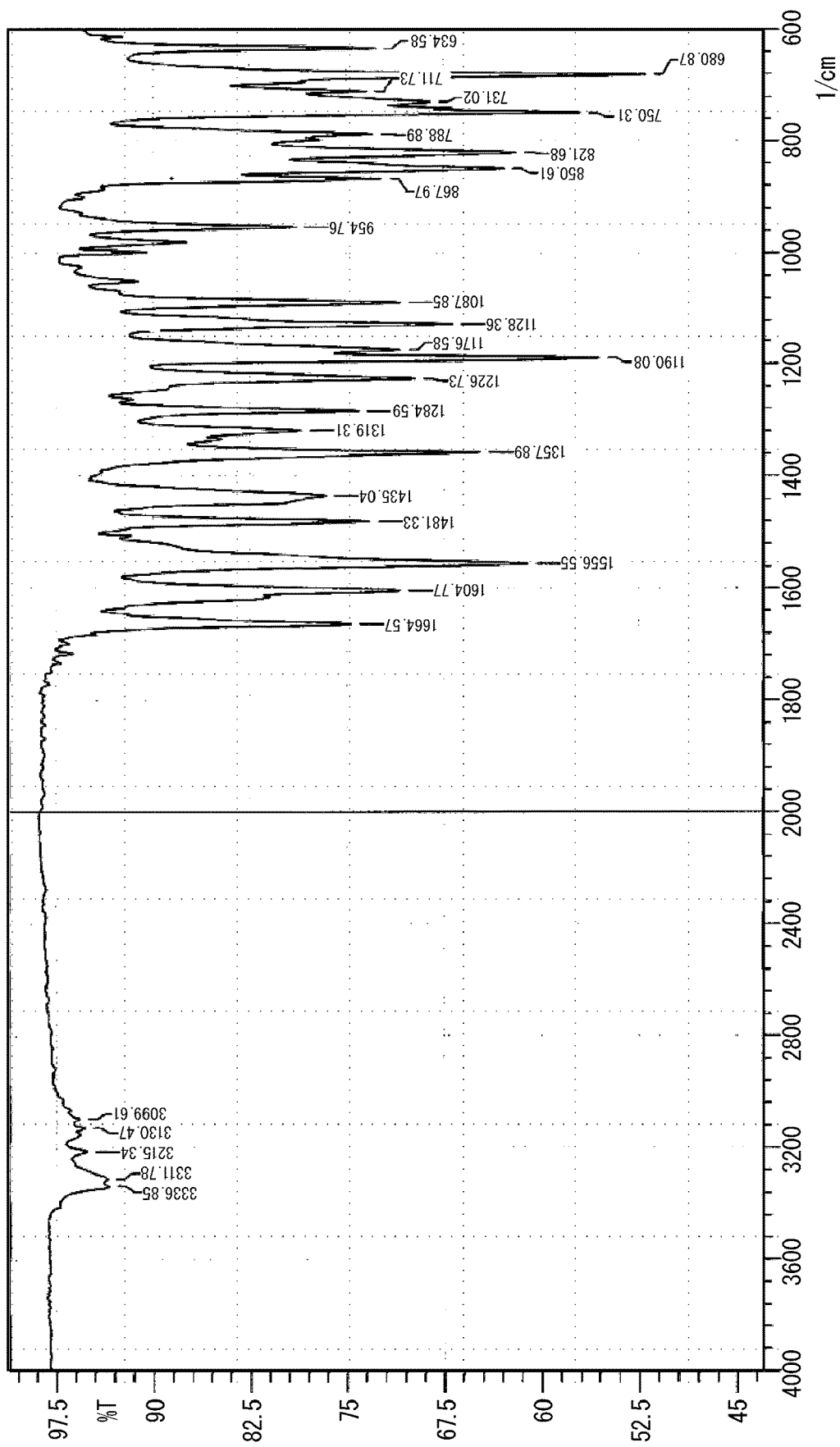
FIG. 8 shows an IR chart of N,N'-di-[3-(benzenesulfonyloxy) phenyl] urea obtained in Synthesis Example 7 according to the present invention.

The product was in the form of white crystals, and had a melting point of 130.9° C. An IR chart thereof is shown in FIG. 8.

Synthesis Example 8

Synthesis of N,N'-di-[(3-benzenesulfonyloxy) phenyl] urea

Crystallization was carried out in the same operations as those of Synthesis Example 7, with the exception of replacing p-toluenesulfonyl chloride used in Synthesis Example 7 with benzenesulfonyl chloride. Crystals were obtained by filtration.

Figure 9:
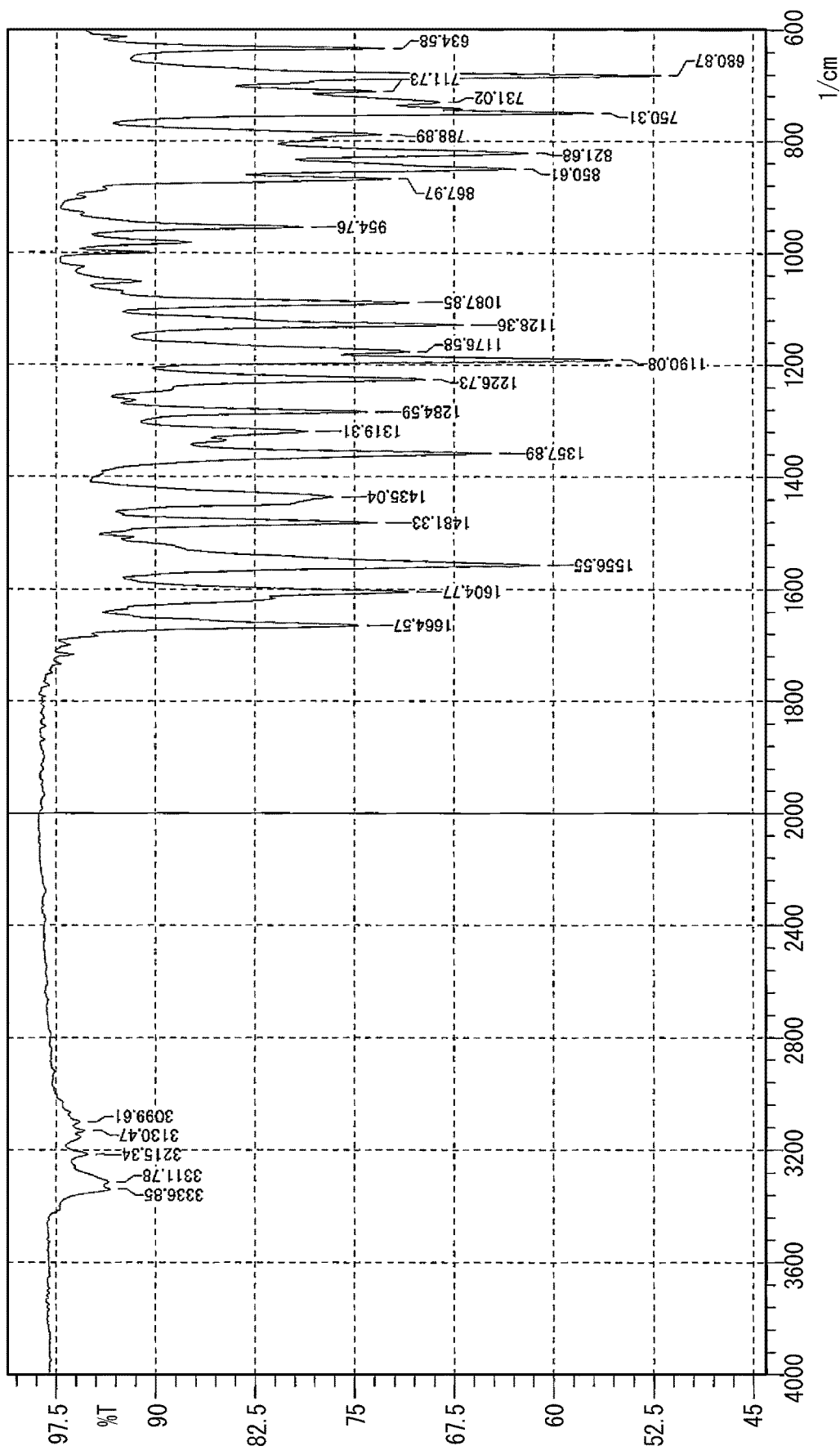
FIG. 9 shows an IR chart of N,N'-di-[3-(benzenesulfonyloxy) phenyl] urea obtained in Synthesis Example 8 according to the present invention.

The melting point was 132° C. to 133° C. An IR chart is shown in FIG. 9.

Synthesis Example 9

Synthesis of N,N'-di-[3-(mesitylenesulfonyloxy) phenyl] urea

N,N'-di-[3-(mesitylenesulfonyloxy) phenyl] urea was obtained by the same operations as those described in Synthesis Example 1, with the exception of replacing 5.26 g of 3-(p-toluenesulfonyloxy) aniline of Synthesis Example 1 with 5.82 g of 3-(mesitylenesulfonyloxy) aniline and replacing N-phenoxycarbonyl-3-(p-toluenesulfonyloxy) aniline with N-phenoxycarbonyl-3-(mesitylenesulfonyloxy) aniline.

Figure 10:
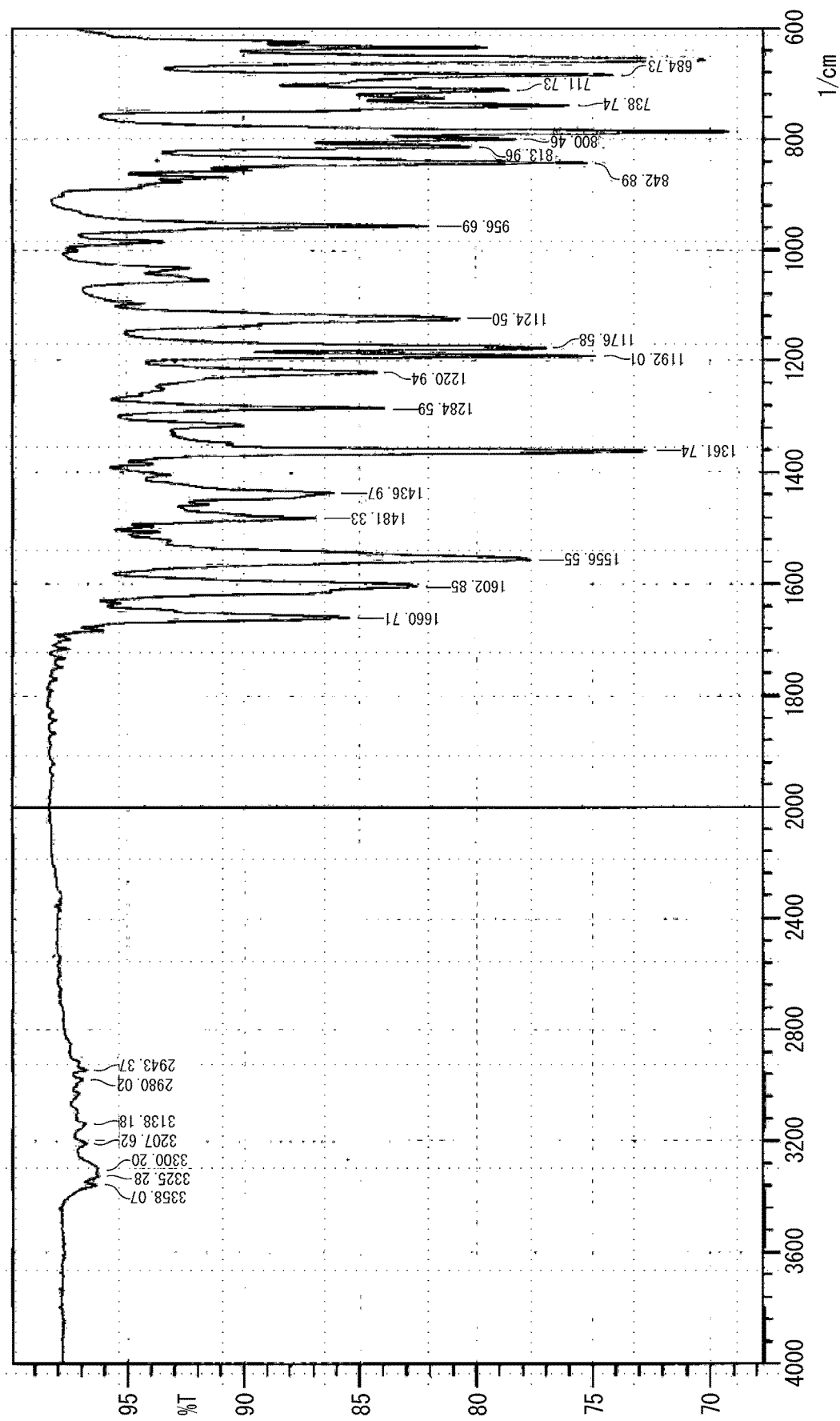
FIG. 10 shows an IR chart of N,N'-di-[3-(mesitylenesulfonyloxy) phenyl] urea obtained in Synthesis Example 9 according to the present invention.

The product was in the form of white crystals and had the melting point of 150.6° C. An IR chart is shown in FIG. 10.

Synthesis Example 10

Synthesis of N,N'-di-[3-(mesitylenesulfonyloxy)] phenylurea

Crystallization was carried out by the same operations as those described in Synthesis Example 3, with the exception of replacing p-toluenesulfonyl chloride used in Synthesis Example 3 with 2,4,6-trimethylbenzenesulfonyl chloride. The crystals were obtained by filtration.

Figure 11:
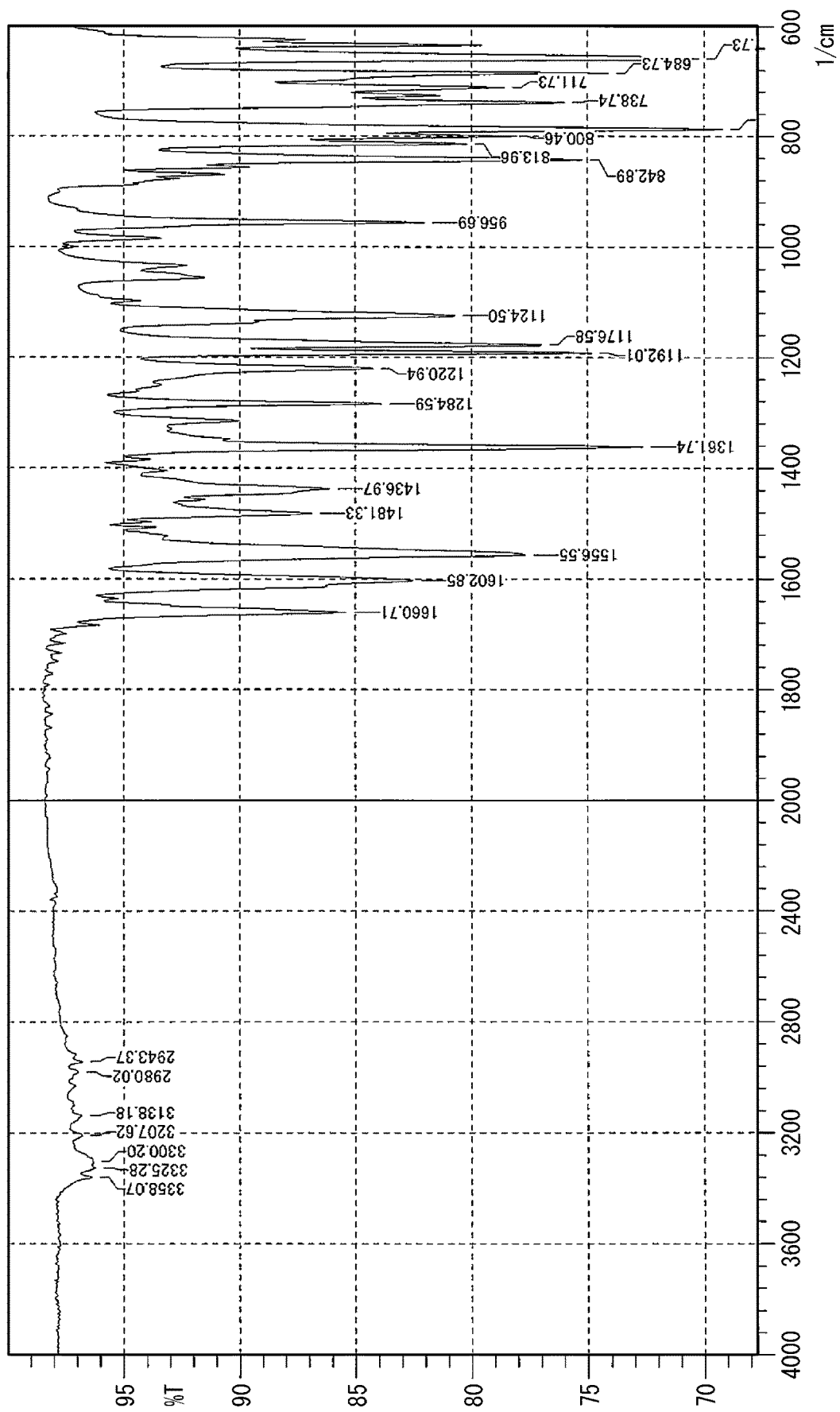
FIG. 11 shows an IR chart of N,N'-di-[3-(mesitylenesulfonyloxy) phenyl] urea obtained in Synthesis Example 10 according to the present invention.

Melting point: 166° C. to 168° C. An IR chart is shown in FIG. 11.

Synthesis Example 11

Synthesis of N,N'-di-[3-(4-ethylbenzenesulfonyloxy) phenyl] urea

The same operations as those described in Synthesis Example 2 were carried out, with the exception of replacing p-toluenesulfonyl chloride used in Synthesis Example 2 with 4-ethylbenzenesulfonyl chloride, to obtain a concentrated residue. Subsequently, methyl alcohol was added to the concentrated residue for crystallization, and filtration was carried out. Thereby, crystals were obtained.

Melting point: 151.4° C. to 152.3° C.

Synthesis Example 12

Synthesis of N,N'-di-[3-(2-naphthalenesulfonyloxy) phenyl] urea

The same operations as those described in Synthesis Example 2 were carried out with the exception of replacing p-toluenesulfonyl chloride used in Synthesis Example 2 with 2-naphthalenesulfonyl chloride, to obtain a concentrated residue. Subsequently, ethyl alcohol was added to the concentrated residue for crystallization, and filtration was carried out. Thereby, crystals were obtained.

Melting point: 156° C. to 160° C.

Synthesis Example 13

Synthesis of N,N'-di-[3-(p-methoxybenzenesulfonyloxy) phenyl] urea

The same operations as those described in Synthesis Example 2 were carried out, with the exception of replacing p-toluenesulfonyl chloride used in Synthesis Example 2 with 4-methoxybenzenebenzenesulfonyl chloride, to obtain a concentrated residue. Methyl alcohol was added to the concentrated residue for crystallization, and filtration was carried out. Thereby, crystals were obtained.

Melting point: 147° C. to 150° C.

Synthesis Example 14

Synthesis of N,N'-di-[3-(benzylsulfonyloxy) phenyl] urea

The same operations as those described in Synthesis Example 2 were carried out, with the exception of replacing p-toluenesulfonyl chloride used in Synthesis Example 2 with benzylsulfonyl chloride, to obtain a concentrated residue. Methyl alcohol was added to the concentrated residue for crystallization, and filtration was carried out. Thereby, crystals were obtained.

Melting point: 163° C. to 165° C.

Synthesis Example 15

Synthesis of N,N'-di-[3-(ethanesulfonyloxy) phenyl] urea

The same operations as those described in Synthesis Example 2 were carried out, with the exception of replacing p-toluenesulfonyl chloride used in Synthesis Example 2 with ethanesulfonyl chloride to obtain a concentrated residue. Methyl alcohol was added to the concentrated residue for crystallization, and filtration was carried out.

Thereby, crystals were obtained.

Melting point: 137° C. to 140° C.

Synthesis Example 16

Synthesis of N,N'-di-[3-(p-toluenesulfonyloxy)-4-methyl-phenyl] urea

The same operations as those described in Synthesis Example 2 were carried out, with the exception of replacing 3-aminophenol used in Synthesis Example 2 with 3-amino-4-methylphenol, to obtain a concentrated residue. Ethyl acetate was added to the concentrated residue for crystallization, and filtration was carried out. Thereby, crystals were obtained.

Melting point: 206.5° C. to 206.9° C.

Synthesis Example 17

Synthesis of N,N'-di-[4-(p-toluenesulfonyloxy) phenyl] urea

The same operations as those described in Synthesis Example 2 were carried out, with the exception of replacing 3-aminophenol used in Synthesis Example 2 with 4-aminophenol, to obtain a concentrated residue. Ethyl acetate was added to the concentrated residue for crystallization, and filtration was carried out. Thereby, crystals were obtained.

Melting point: 179° C. to 180° C.

Synthesis Example 18

Synthesis of N,N'-di-[4-(benzenesulfonyloxy) phenyl] urea

The same operations as those described in Synthesis Example 2 were carried out, with the exception of replacing p-toluenesulfonyl chloride used in Synthesis Example 2 with benzenesulfonyl chloride, to obtain a concentrated residue. Ethyl alcohol was added to the concentrated residue for crystallization, and filtration was carried out. Thereby, crystals were obtained.

Melting point: 154° C. to 156° C.

Synthesis Example 19

Synthesis of N,N'-di-[4-(ethanesulfonyloxy) phenyl] urea

The same operations as those described in Synthesis Example 2 were carried out, with the exception of replacing p-toluenesulfonyl chloride used in Synthesis Example 2 with ethanesulfonyl chloride, to obtain a concentrated residue. Ethyl acetate was added to the concentrated residue for crystallization, and filtration was carried out. Thereby, crystals were obtained.

Melting point: 165.8° C. to 166.8° C.

Synthesis Example 20

Synthesis of N,N'-di-[2-(p-toluenesulfonyloxy)] phenylurea

A four-necked flask equipped with a thermometer, a stirrer, and a nitrogen introducing tube was charged with 10.9 g of 2-aminophenol, 3.03 g of urea and 40 g of butyl acetate. The mixture was heated under a nitrogen atmosphere.

The reaction mixture was stirred for 10 hours at 125° C. During the reaction, crystals were precipitated, but the reaction was continued by stirring as it was. After the crystals were separated by filtration, the material dissolved in ethyl acetate was subjected to column chromatography using silica gel. Thereby, 2,2'-dihydroxydiphenylurea was obtained.

2,2'-Dihydroxydiphenylurea, ethyl acetate, and p-toluenesulfonyl chloride were charged, and the internal temperature was set to 70° C. Subsequently, triethylamine was added thereto dropwise to carry out the reaction.

After completion of the reaction, water was added for liquid separation, and the organic layer was concentrated. Thereby, crystals were solidified. The crystals were further subjected to column chromatography using silica gel to obtain N,N'-di-[2-(p-toluenesulfonyloxy)] phenylurea.

Melting point: 156° C. to 160° C.

The obtained crystals indicated two endothermic peaks at 143.7° C. and 162.5° C. and an exothermic peak at 149.6° C. according to thermal analysis.

Some developers may be decomposed due to the reaction with water, so that the original developing ability may be impaired in some cases. In order to confirm the stability of the synthesized compounds of the present invention with respect to water (that is, decomposition resistance to water), the synthesized compound was dissolved at a concentration of 0.5% in a mixture of acetonitrile and water (acetonitrile/water=80/20). The mixture was stirred at 50° C. for 5 hours, and the amount of decomposed products was measured by means of high performance liquid chromatography (detection wavelength: 205 nm) manufactured by Shimadzu Corporation.

When the amount of decomposed products was 10% or more, the decomposition resistance to water was set to X. On the other hand, when the amount of decomposed products was 1% or less, the decomposition resistance to water was set to 0.

A thermosensitive recording material was prepared by the operations described below.

[Preparation of Coating Material for Undercoat]

100 parts of plastic hollow particles (trade name: ROPAQUE SN-1055: hollow ratio: 55%, and solid content 26.5%), 100 parts of calcined kaolin in the form of a 50% dispersion liquid, 25 parts of styrene-butadiene-based latex (trade name: L-1571, solid content 48%), 50 parts of a 10% aqueous solution of oxidized starch, and 20 parts of water were mixed to prepare a coating material for an undercoat.

Example 1

| [Preparation of Coating Material for Use in Thermosensitive Recording] | |
|---|---|
| Liquid A (Preparation of Dye Dispersion Liquid) | |
| 3-(N,N-dibutylamino)-6-methyl-7-anilinofluoran | 10 parts |
| 10% aqueous solution of polyvinyl alcohol | 10 parts |
| Water | 16.7 parts |
| Liquid B (Preparation of Developer Dispersion Liquid) | |
| N,N'-di-[3-(p-toluenesulfonyloxy) phenyl] urea (Synthesis Example 1) | 20 parts |
| 10% aqueous solution of polyvinyl alcohol | 20 parts |
| Water | 33.3 parts |
| Liquid C (Preparation of Sensitizer Dispersion Liquid) | |
| 1,2-bis(m-tolyloxy) ethane | 15 parts |
| 10% aqueous solution of polyvinyl alcohol | 15 parts |
| Water | 25 parts |

Dispersion liquids of the aforementioned Liquid A, Liquid B, and Liquid C were pulverized by a sand grinder until the average particle diameter became 1 μm or less, and each of the dispersion liquids was mixed at the ratio described below to prepare a coating liquid.

| | |
|---|---|
| Liquid A (dye dispersion liquid) | 36.7 parts |
| Liquid B (developer dispersion liquid) | 73.3 parts |
| Liquid C (sensitizer dispersion liquid) | 55.0 parts |

A composition formed of 27 parts of aluminum hydroxide (trade name: Higilite H-42), 10 parts of amorphous silica (trade name: Mizukasil P-527), 100 parts of a 10% lysate of oxidized starch, 19.4 parts of zinc stearate dispersion liquid: (trade name: Hydrin Z-8-36), and 50 parts of water was mixed to prepare a coating material for use in thermosensitive recording.

[Preparation of Thermo Sensitive Recording Material]

A coating material for use in an undercoat was applied and dried on high quality paper (acidic paper) having a basis weight of 53 g as a base sheet such that the mass per area was 6 g/m$^2$ after drying. Subsequently, a thermosensitive coating material was applied thereon and dried so that the mass per area was 3.8 g/m$^2$ after drying.

The sheet obtained above was treated with a supercalender such that the smoothness (JIS P 8155: 2010) was in the range of from 900 to 1200 s. Thereby, a thermosensitive recording material was prepared.

[Various Tests]

1. Thermo Sensitive Recording Test (Color Development Test)

The thermosensitive recording material prepared above was subjected to an applied energy of 0.24 mJ/dot and 0.38 mJ/dot using a thermosensitive recording paper printing tester (TH-PMD manufactured by Okura Electric Co., Ltd.). The print density of the recorded portion was measured with a Macbeth reflection densitometer RD-914.

With respect to the sensitivity test, evaluation was carried out with a printing density at the low energy of the applied energy of 0.24 mJ/dot.

On the other hand, the printed portion to which the applied energy of 0.38 mJ/dot was applied was used in the storage stability tests for heat resistance, moist heat resistance, light resistance, oil resistance, water resistance and plasticizer resistance, described below.

2. Heat Resistance Test

The thermosensitive recording material recorded with the applied energy of 0.38 mJ/dot in the thermosensitive recording test was left for 24 hours under a constant temperature environment at a test temperature of 60° C., and subsequently, the image density of the printed portion of the test piece and the density of the unprinted portion were measured with a Macbeth reflection densitometer.

3. Moist Heat Resistance Test

The thermosensitive recording material recorded with the applied energy of 0.38 mJ/dot in the thermosensitive recording test was left for 24 hours under an environment of a test temperature of 40° C. and 90% RH, and subsequently, the image density of the printed portion of the test piece and the density of the unprinted portion were measured with a Macbeth reflection densitometer.

4. Light Resistance Test

The thermosensitive recording material recorded with the applied energy of 0.38 mJ/dot in the thermosensitive recording test was exposed to 5,000 Lux for 100 hours, and subsequently, the image density was measured with a Macbeth reflection densitometer.

5. Oil Resistance Test

The thermosensitive recording material recorded with the applied energy of 0.38 mJ/dot in the thermosensitive recording test was immersed in salad oil for 10 minutes. Subsequently, the oil adhered to the test piece was wiped off, and the image density was measured with a Macbeth reflection densitometer.

6. Water Resistance Test

The thermosensitive recording material recorded with the applied energy of 0.38 mJ/dot in the thermosensitive recording test was immersed in water for 15 hours. Subsequently, the test piece was air-dried, and the image density and the unprinted portion density were measured with a Macbeth reflection densitometer.

7. Plasticizer Resistance Test

A wrap film (trade name: HIGH WRAP KMA, manufactured by Mitsui Chemicals, Incorporated) was applied three times on a polycarbonate pipe (48 mm φ), and a thermosensitive recording material recorded with the applied energy of 0.38 mJ/dot in the thermosensitive recording test was placed thereon. The wrap film was further applied three times on top of the paper and left to stand for 24 hours under an environment of 20° C. and 65% RH. Subsequently, the image density and the unprinted portion density were measured with a Macbeth reflection densitometer.

The results are shown in Table 1.

Example 2

The same operations as those described in Example 1 were carried out, with the exception of replacing the N,N'-di-[3-(p-toluenesulfonyloxy) phenyl] urea in Liquid B of Example 1 with Sample 1 of Synthesis Example 2.

The various test results of the thermosensitive recording material according to the present example were as shown in Table 1.

Example 3

The same operations as those described in Example 1 were carried out, with the exception of replacing the N,N'-di-[3-(p-toluenesulfonyloxy) phenyl] urea in Liquid B of Example 1 with Sample 2 of Synthesis Example 2.

The various test results of the thermosensitive recording material according to the present example were as shown in Table 1.

Example 4

The same operations as those described in Example 1 were carried out, with the exception of replacing the N,N'-di-[3-(p-toluenesulfonyloxy) phenyl] urea in Liquid B of Example 1 with Sample 3 of Synthesis Example 2.

The various test results of the thermosensitive recording material according to the present example were as shown in Table 1.

Example 5

The same operations as those described in Example 1 were carried out, with the exception of replacing the N,N'-di-[3-(p-toluenesulfonyloxy) phenyl] urea in Liquid B of Example 1 with the compound of Synthesis Example 4.

The various test results of the thermosensitive recording material according to the present example were as shown in Table 1.

Example 6

The same operations as those described in Example 1 were carried out, with the exception of replacing the N,N'-di-[3-(p-toluenesulfonyloxy) phenyl] urea in Liquid B of Example 1 with N,N'-di-[3-(o-toluenesulfonyloxy) phenyl] urea (Synthesis Example 6).

The various test results of the thermosensitive recording material according to the present example were as shown in Table 1.

Example 7

The same operations as those described in Example 1 were carried out, with the exception of replacing the N,N'-di-[3-(p-toluenesulfonyloxy) phenyl] urea in Liquid B of Example 1 with N,N'-di-[3-(benzenesulfonyloxy) phenyl] urea (Synthesis Example 7).

The various test results of the thermosensitive recording material according to the present example were as shown in Table 1.

Example 8

The same operations as those described in Example 1 were carried out, with the exception of replacing the N,N'-di-[3-(p-toluenesulfonyloxy) phenyl] urea in Liquid B of Example 1 with N,N'-di-[3-(benzenesulfonyloxy) phenyl] urea (Synthesis Example 8).

The various test results of the thermosensitive recording material according to the present example were as shown in Table 1.

Example 9

The same operations as those described in Example 1 were carried out, with the exception of replacing the N,N'-di-[3-(p-toluenesulfonyloxy) phenyl] urea in Liquid B of Example 1 with N,N'-di-[3-(mesitylenesulfonyloxy) phenyl] urea (Synthesis Example 9).

The various test results of the thermosensitive recording material according to the present example were as shown in Table 1.

Example 10

The same operations as those described in Example 1 were carried out, with the exception of replacing the N,N'-di-[3-(p-toluenesulfonyloxy) phenyl] urea in Liquid B of Example 1 with N,N'-di-[3-(mesitylenesulfonyloxy) phenyl] urea (Synthesis Example 10).

The various test results of the thermosensitive recording material according to the present example were as shown in Table 1.

Example 11

The same operations as those described in Example 1 were carried out, with the exception of replacing the N,N'-di-[3-(p-toluenesulfonyloxy) phenyl] urea in Liquid B of Example 1 with N,N'-di-[3-(2-naphthalenesulfonyloxy) phenyl] urea (Synthesis Example 12).

The various test results of the thermosensitive recording material according to the present example were as shown in Table 1.

Example 12

The same operations as those described in Example 1 were carried out, with the exception of replacing the N,N'-di-[3-(p-toluenesulfonyloxy) phenyl] urea in Liquid B of Example 1 with N,N'-di-[3-(p-methoxybenzenesulfonyloxy) phenyl] urea (Synthesis Example 13).

The various test results of the thermosensitive recording material according to the present example were as shown in Table 2.

Example 13

The same operations as those described in Example 1 were carried out, with the exception of replacing the N,N'-di-[3-(p-toluenesulfonyloxy) phenyl] urea in Liquid B of Example 1 with N,N'-di-[3-(benzenesulfonyloxy) phenyl] urea (Synthesis Example 14).

The various test results of the thermosensitive recording material according to the present example were as shown in Table 2.

Example 14

The same operations as those described in Example 1 were carried out, with the exception of replacing the N,N'-di-[3-(p-toluenesulfonyloxy) phenyl] urea in Liquid B of Example 1 with N,N'-di-[3-(ethanesulfonyloxy) phenyl] urea (Synthesis Example 15). The various test results of the thermosensitive recording material according to the present example were as shown in Table 2.

Example 15

The same operations as those described in Example 1 were carried out, with the exception of replacing the N,N'-di-[3-(p-toluenesulfonyloxy) phenyl] urea in Liquid B of Example 1 with N,N'-di-[4-(p-toluenesulfonyloxy) phenyl] urea (Synthesis Example 17).

The various test results of the thermosensitive recording material according to the present example were as shown in Table 2.

Example 16

The same operations as those described in Example 1 were carried out, with the exception of replacing the N,N'-di-[3-(p-toluenesulfonyloxy) phenyl] urea in Liquid B of Example 1 with N,N'-di-[4-(benzenesulfonyloxy) phenyl] urea (Synthesis Example 18).

The various test results of the thermosensitive recording material according to the present example were as shown in Table 2.

Comparative Example 1

The same operations as those described in Example 1 were carried out, with the exception of replacing the N,N'-di-[3-(p-toluenesulfonyloxy) phenyl] urea in Liquid B of Example 1 with 4,4'-isopropylidenediphenol (bisphenol A). The various test results of the thermosensitive recording material according to the present reference example were as shown in Table 2.

Comparative Example 2

The same operations as those described in Example 1 were carried out, with the exception of replacing the N,N'-di-[3-(p-toluenesulfonyloxy) phenyl] urea in Liquid B of Example 1 with 4,4'-dihydroxydiphenylsulfone (bisphenol S). The various test results of the thermosensitive recording material according to the present reference example were as shown in Table 2.

Comparative Example 3

The same operations as those described in Example 1 were carried out, with the exception of replacing the N,N'-di-[3-(p-toluenesulfonyloxy) phenyl] urea in Liquid B of Example 1 with 4-allyloxy-4'-hydroxydiphenylsulfone. The various test results of the thermosensitive recording material according to the present reference example were as shown in Table 2.

Comparative Example 4

The same operations as those described in Example 1 were carried out, with the exception of replacing the N,N'-di-[3-(p-toluenesulfonyloxy) phenyl] urea in Liquid B of Example 1 with 4-hydroxy-4'-isopropyloxy-diphenylsulfone. The various test results of the thermosensitive recording material according to the present reference example were as shown in Table 2.

Comparative Example 5

The same operations as those described in Example 1 were carried out, with the exception of replacing the N,N'-di-[3-(p-toluenesulfonyloxy) phenyl] urea in Liquid B of Example 1 with N-3-(p-toluenesulfonyloxy) phenyl-N'-(p-toluenesulfonyl)-urea. The various test results of the thermosensitive recording material according to the present reference example were as shown in Table 2.

Comparative Example 6

The same operations as those described in Example 1 were carried out, with the exception of replacing the N,N'-di-[3-(p-toluenesulfonyloxy) phenyl] urea in Liquid B of Example 1 with N-(2-(3-phenylureido) phenyl)-benzenesulfonamide. The various test results of the thermosensitive recording material according to the present reference example were as shown in Table 2.

As is apparent from the Examples and Tables, the thermosensitive recording materials prepared from the N,N'-diarylurea derivatives of the present invention exhibited a good color density with a high whiteness, and also exhibited good results in all the preservability tests of heat resistance, moisture resistance, light resistance, water resistance, oil resistance and plasticizer resistance in the printed portion.

TABLE 1

| Test Example | Developer | Decomposability to water | Measurement portion | Coloring density 0.24 mJ | Coloring density 0.38 mJ | Moist heat resistance | Heat resistance | Light resistance | Water resistance | Oil resistance | Plasticizer resistance |
|---|---|---|---|---|---|---|---|---|---|---|---|
| Example 1 | N,N'-di-[3-(p-toluenesulfonyloxy)phenyl] urea | ○ | Unprinted portion | 0.05 | 0.05 | 0.05 | 0.05 | 0.05 | 0.05 | 0.05 |
| | | | Printed portion | 1.06 | 1.25 | 1.23 | 1.19 | 1.23 | 1.18 | 1.04 | 0.55 |
| Example 2 | N,N'-di-[3-(p-toluenesulfonyloxy)phenyl] urea, Sample 1 | ○ | Unprinted portion | 0.05 | 0.05 | 0.05 | 0.05 | 0.05 | 0.05 | 0.05 |
| | | | Printed portion | 1.09 | 1.25 | 1.22 | 1.19 | 1.23 | 1.19 | 1.04 | 0.56 |
| Example 3 | N,N'-di-[3-(p-toluenesulfonyloxy)phenyl] urea, Sample 2 | ○ | Unprinted portion | 0.05 | 0.05 | 0.05 | 0.05 | 0.05 | 0.05 | 0.05 |
| | | | Printed portion | 1.08 | 1.24 | 1.23 | 1.19 | 1.23 | 1.18 | 1.02 | 0.54 |
| Example 4 | N,N'-di-[3-(p-toluenesulfonyloxy)phenyl] urea, Sample 3 | ○ | Unprinted portion | 0.05 | 0.05 | 0.05 | 0.05 | 0.05 | 0.05 | 0.05 |
| | | | Printed portion | 1.09 | 1.26 | 1.23 | 1.20 | 1.23 | 1.19 | 1.05 | 0.57 |
| Example 5 | N,N'-di-[3-(p-toluenesulfonyloxy)phenyl] urea, Sample 4 | ○ | Unprinted portion | 0.05 | 0.05 | 0.06 | 0.05 | 0.05 | 0.05 | 0.05 |
| | | | Printed portion | 1.12 | 1.26 | 1.23 | 1.19 | 1.23 | 1.20 | 1.02 | 0.58 |
| Example 6 | N,N'-di-[3-(o-toluenesulfonyloxy)phenyl] urea | ○ | Unprinted portion | 0.05 | 0.05 | 0.05 | 0.05 | 0.05 | 0.05 | 0.05 |
| | | | Printed portion | 1.11 | 1.26 | 1.19 | 1.20 | 1.23 | 1.21 | 1.05 | 0.65 |
| Example 7 | N,N'-di-[3-(benzenesulfonyloxy)phenyl] urea | ○ | Unprinted portion | 0.05 | 0.05 | 0.05 | 0.05 | 0.05 | 0.05 | 0.05 |
| | | | Printed portion | 1.02 | 1.24 | 1.22 | 1.17 | 1.21 | 1.17 | 1.01 | 0.51 |
| Example 8 | N,N'-di-[3-(benzenesulfonyloxy)phenyl] urea | ○ | Unprinted portion | 0.05 | 0.05 | 0.05 | 0.05 | 0.05 | 0.05 | 0.05 |
| | | | Printed portion | 1.05 | 1.25 | 1.23 | 1.16 | 1.20 | 1.16 | 0.99 | 0.49 |
| Example 9 | N,N'-di-[3-(mesitylenesulfonyloxy)phenyl] urea | ○ | Unprinted portion | 0.05 | 0.05 | 0.05 | 0.05 | 0.05 | 0.05 | 0.05 |
| | | | Printed portion | 1.01 | 1.25 | 1.24 | 1.21 | 1.22 | 1.16 | 1.00 | 0.50 |
| Example 10 | N,N'-di-[3-(mesitylenesulfonyloxy)phenyl] urea | ○ | Unprinted portion | 0.05 | 0.05 | 0.05 | 0.05 | 0.05 | 0.05 | 0.05 |
| | | | Printed portion | 1.01 | 1.27 | 1.24 | 1.20 | 1.24 | 1.18 | 1.02 | 0.54 |
| Example 11 | N,N'-di-[3-(2-naphthalenesulfonyloxy)phenyl] urea | ○ | Unprinted portion | 0.05 | 0.05 | 0.05 | 0.05 | 0.05 | 0.05 | 0.05 |
| | | | Printed portion | 1.03 | 1.26 | 1.23 | 1.20 | 1.24 | 1.21 | 1.05 | 0.48 |

TABLE 2

| Test Example | Developer | Decomposability to water | Measurement portion | Coloring density 0.24 mJ | Coloring density 0.38 mJ | Moist heat resistance | Heat resistance | Light resistance | Water resistance | Oil resistance | Plasticizer resistance |
|---|---|---|---|---|---|---|---|---|---|---|---|
| Example 12 | N,N'-di-[3-(p-methoxybenzene-sulfonyloxy) phenyl] urea | ○ | Unprinted portion | 0.05 | 0.05 | 0.05 | 0.05 | 0.05 | 0.05 | 0.05 | 0.05 |
| | | | Printed portion | 0.96 | 1.25 | 1.20 | 1.21 | 1.24 | 1.09 | 0.92 | 0.46 |
| Example 13 | N,N'-di-[3-(benzylsulfonyloxy) phenyl] urea | ○ | Unprinted portion | 0.05 | 0.05 | 0.05 | 0.05 | 0.05 | 0.05 | 0.05 | 0.05 |
| | | | Printed portion | 1.09 | 1.26 | 1.23 | 1.18 | 1.24 | 1.21 | 1.05 | 0.48 |
| Example 14 | N,N'-di-[3-(ethanesulfonyloxy) phenyl] urea | ○ | Unprinted portion | 0.05 | 0.05 | 0.05 | 0.05 | 0.05 | 0.05 | 0.05 | 0.05 |
| | | | Printed portion | 1.11 | 1.25 | 1.19 | 1.15 | 1.23 | 1.04 | 0.91 | 0.44 |
| Example 15 | N,N'-di-[4-(p-toluenesulfonyloxy) phenyl] urea | ○ | Unprinted portion | 0.05 | 0.05 | 0.05 | 0.05 | 0.05 | 0.05 | 0.05 | 0.05 |
| | | | Printed portion | 1.04 | 1.26 | 1.23 | 1.18 | 1.24 | 1.21 | 0.91 | 0.48 |
| Example 16 | N,N'-di-[4-(benzenesulfonyloxy) phenyl] urea | ○ | Unprinted portion | 0.05 | 0.05 | 0.05 | 0.05 | 0.05 | 0.05 | 0.05 | 0.05 |
| | | | Printed portion | 1.12 | 1.28 | 1.23 | 1.22 | 1.23 | 1.21 | 1.08 | 0.70 |
| Comparative Example 1 | 4,4'-isopropylidene-diphenol | ○ | Unprinted portion | 0.05 | 0.06 | 0.06 | 0.05 | 0.04 | 0.06 | 0.06 | |
| | | | Printed portion | 0.95 | 1.25 | 1.22 | 1.02 | 1.22 | 0.71 | 0.08 | 0.06 |
| Comparative Example 2 | 4,4'-dihydroxy-diphenylsulfone | ○ | Unprinted portion | 0.05 | 0.04 | 0.05 | 0.05 | 0.05 | 0.04 | 0.04 | |
| | | | Printed portion | 0.45 | 1.11 | 1.14 | 0.95 | 1.08 | 0.83 | 0.89 | 0.21 |
| Comparative Example 3 | 4-allyloxy-4'-hydroxydiphenyl-sulfone | ○ | Unprinted portion | 0.04 | 0.04 | 0.04 | 0.04 | 0.04 | 0.04 | 0.04 | |
| | | | Printed portion | 0.89 | 1.25 | 0.91 | 0.44 | 1.19 | 0.81 | 0.11 | 0.06 |
| Comparative Example 4 | 4-hydroxy-4'-isopropyloxy-diphenylsulfone | ○ | Unprinted portion | 0.05 | 0.05 | 0.05 | 0.05 | 0.05 | 0.04 | 0.04 | |
| | | | Printed portion | 0.93 | 1.19 | 1.15 | 1.11 | 1.08 | 0.83 | 0.89 | 0.21 |
| Comparative Example 5 | N-3-[(p-toluene-sulfonyloxy) phenyl]-N'-(p-toluenesulfonyl) urea | X | Unprinted portion | 0.05 | 0.05 | 0.05 | 0.05 | 0.05 | 0.05 | 0.05 | 0.05 |
| | | | Printed portion | 0.91 | 1.26 | 1.26 | 1.22 | 1.22 | 1.09 | 1.03 | 0.51 |
| Comparative Example 6 | N-[2-(3-pheylureido) phenyl]-benzenesulfonamide | ○ | Unprinted portion | 0.04 | 0.04 | 0.05 | 0.04 | 0.05 | 0.04 | 0.04 | |
| | | | Printed portion | 0.84 | 1.21 | 1.20 | 1.13 | 1.22 | 1.05 | 0.12 | 0.28 |

INDUSTRIAL APPLICABILITY

In the thermo sensitive recording materials of the present invention, the developer to be used is the N,N'-diarylurea derivative represented by the general formula (1). For this reason, there is no concern of endocrine disruption, and there is no decomposition by water. In addition, the superior color density is exhibited, the whiteness in the non-printed portion is high, and good storability can be obtained in all storability tests. Therefore, the industrial applicability as an alternative to conventional thermo sensitive recording materials is extremely promising.

What is claimed is:

1. An N,N'-diarylurea derivative of Formula (1):

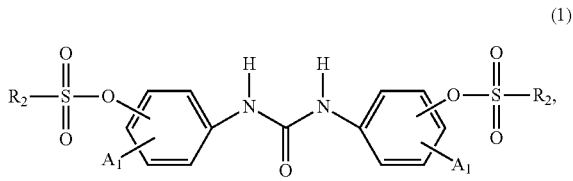

wherein each $R_2$ is independently:
an unsubstituted linear, branched or alicyclic alkyl group having 1 to 12 carbon atoms,
an aralkyl group having 7 to 12 carbon atoms, or
an aryl group having 6 to 12 carbon atoms,
wherein the aralkyl group and the aryl group are independently optionally substituted with an alkyl group having 1 to 12 carbon atoms, an alkoxy group having 1 to 12 carbon atoms, an aryl group having 6 to 12 carbon atoms, or a halogen atom; and
wherein each $A_1$ is a hydrogen atom.

2. The N,N'-diarylurea derivative according to claim 1, which is represented by the following general formula (3):

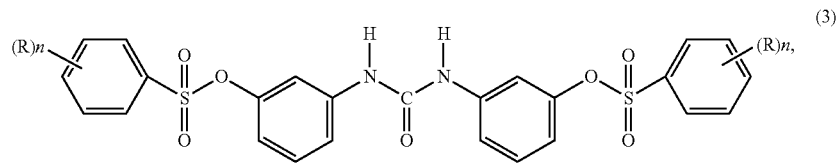
(3)

wherein n represents an integer ranging from 0 to 3, when n represents an integer from 1 to 3, R represents an alkyl group having 1 to 12 carbon atoms.

3. A method for producing the N,N'-diarylurea derivative as recited in claim 1, comprising:
reacting a compound represented by the following general formula (4):

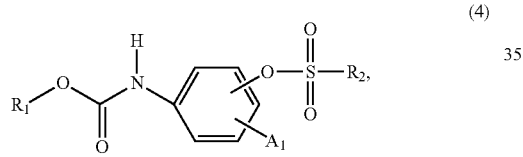
(4)

with an aromatic amine compound represented by the following general formula (5):

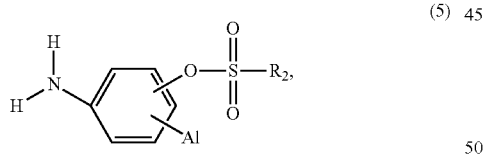
(5)

wherein $R_1$ represents an alkyl group or an aryl group, and $R_2$ and $A_1$ are defined as in claim 1.

4. A method for producing the N,N'-diarylurea derivative as recited in claim 2, comprising:
reacting a compound represented by the following general formula (6):

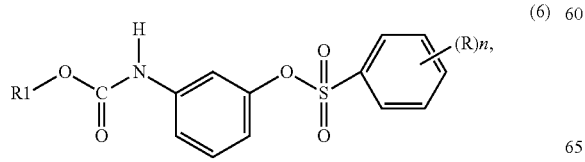
(6)

with an aromatic amine compound represented by the following general formula (7):

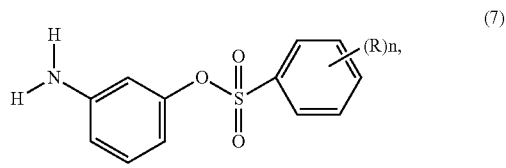
(7)

wherein $R_1$ represents an alkyl group or an aryl group, and R and n are defined as in claim 2.

5. A method for producing the N,N'-diarylurea derivative as recited in claim 1, comprising:
reacting a dihydroxydiphenylurea represented by the following general formula (8):

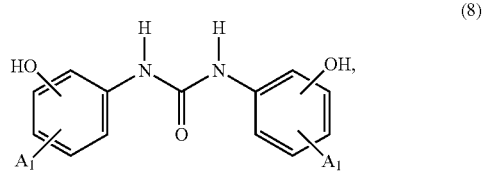
(8)

with a sulfonating agent represented by the following general formula (9):

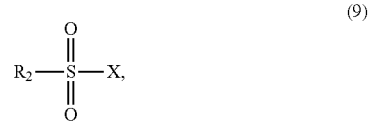
(9)

in the presence of an aprotic solvent, wherein $R_2$ and $A_1$ are defined as in claim 1, and X is a halogen atom.

6. A method for producing the N,N'-diarylurea derivative as recited in claim 1, comprising:
reacting an aminophenol compound represented by the following general formula (8-1):

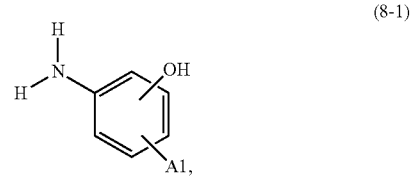
(8-1)

with urea in the presence of an aprotic solvent, and subsequently reacting with a sulfonating agent represented by the following general formula (9):

(9)

wherein $R_2$ and $A_1$ are defined in claim 1, and X is a halogen atom.

7. The method for producing the N,N'-diarylurea derivative according to claim 5, wherein the aprotic solvent is butyl acetate, amyl acetate, isoamyl acetate, toluene or xylene.

8. The method for producing the N,N'-diarylurea derivative according to claim 6, wherein the aprotic solvent is butyl acetate, amyl acetate, isoamyl acetate, toluene or xylene.

9. The N,N'-diarylurea derivative according to claim 1, wherein each $R_2$ is independently: an aralkyl group having 7 to 12 carbon atoms, or an aryl group having 6 to 12 carbon atoms that are independently optionally substituted with an alkyl group having 1 to 12 carbon atom, an alkoxy group having 1 to 12 carbon atoms or an aryl group having 6 to 12 carbon atoms.

10. A thermosensitive recording material comprising the N,N'-diarylurea derivative as recited in claim 1, and at least one selected from the group consisting of N-[2-(3-phenylureido)phenyl]-benzenesulfonamide and N-3-[(p-toluenesulfonyl)oxy] phenyl-N'-(p-toluenesulfonyl)-urea.

11. The thermosensitive recording material of claim 10, wherein the N,N'-diarylurea derivative is represented by the following general formula (3):

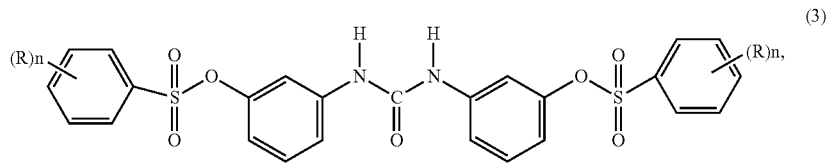
(3)

wherein n represents an integer ranging from 0 to 3, when n represents an integer from 1 to 3, R represents an alkyl group.

* * * * *